(12) United States Patent
Ishibashi

(10) Patent No.: US 8,628,942 B2
(45) Date of Patent: Jan. 14, 2014

(54) METHOD FOR PREPARING TETRAPYRROLE COMPOUNDS AND TETRAPYRROLE COMPOUNDS

(75) Inventor: Toru Ishibashi, Nagasaki (JP)

(73) Assignee: Hirofumi Fukutome, Fukuoka (JP)

( * ) Notice: Subject to any disclaimer, the term of this patent is extended or adjusted under 35 U.S.C. 154(b) by 38 days.

(21) Appl. No.: 12/743,774

(22) PCT Filed: Dec. 1, 2008

(86) PCT No.: PCT/JP2008/071828
§ 371 (c)(1),
(2), (4) Date: Jun. 17, 2010

(87) PCT Pub. No.: WO2009/069806
PCT Pub. Date: Jun. 4, 2009

(65) Prior Publication Data
US 2010/0280236 A1    Nov. 4, 2010

(30) Foreign Application Priority Data

Nov. 30, 2007 (JP) ................................. 2007-310116

(51) Int. Cl.
*C12P 17/16* (2006.01)
(52) U.S. Cl.
USPC ........................................................ 435/118
(58) Field of Classification Search
USPC ........................................................ 435/118
See application file for complete search history.

(56) References Cited

FOREIGN PATENT DOCUMENTS

| | | |
|---|---|---|
| EP | 2332648 A1 | 6/2011 |
| JP | 05-038295 A | 2/1993 |
| JP | 05-091866 A | 4/1993 |
| JP | 05-244937 A | 9/1993 |
| JP | 11-255790 A | 9/1999 |
| JP | 2000-023691 A | 1/2000 |

OTHER PUBLICATIONS

JD23504 available from National Bio-Resources (date unknown).*
Chen S. L. et al, Database UniProtKB/TrEMBL, May 16, 2006, Accession No. Q1R8B4, retrieval date Jan. 14, 2009.
Cox, R. and Charles, H.P., Porphyrin-accumulating mutants of *Escherichia coli*, J. Bacteriol., 1973, vol. 113, No. 1, pp. 122-132.
Yang, H. et al, Non-iron porphyrins cause tumbling to blue light by an *Escherichia coli* mutant defective in hemG, Proc. Natl. Acad. Sci. USA, 1996, vol. 93, pp. 2459-2463.
Borovkov, V.V. et al, Convenient method for efficient iron and manganese ion insertion into various porphyrins under mild conditions, Synlett., 1999, No. 1, pp. 61-62.
Mariana B. Spesia et al; Photoinactivation of *Escherichia coli* Using Porphyrin Derivatives with Different No. of Cationic Charges; FEMS Immunology and Medical Microbiology 44 (2005) 289-295; published Jan. 7, 2005.
Margrethe H. Serres et al; A Functional Update of the *Escherichia coli* K-12 Genome; Genome Biology vol. 2 No. 9; pp. 0035.1-0035.7; published Aug. 20, 2001.
English language translation of Russian Office Action; Application No. 2010126588; dated Dec. 1, 2008.
Europeon Search Report; Application No. EP 08853739.4.

* cited by examiner

*Primary Examiner* — Tekchand Saidha
(74) *Attorney, Agent, or Firm* — Arent Fox LLP

(57) ABSTRACT

A tetrapyrrole compound is prepared by cultivating bacterial cells of *Escherichia coli*, which cannot express the gene ypjD (b2611) due to the variation thereof, in a culture medium and obtaining the resulting tetrapyrrole compound having a porphyrin ring structure from the culture medium.

4 Claims, 22 Drawing Sheets

METHOD FOR PREPARING TETRAPYRROLE COMPOUNDS AND TETRAPYRROLE COMPOUNDS

TECHNICAL FIELD

The present invention relates to a method for the preparation of a tetrapyrrole compound and the resulting tetrapyrrole compound.

BACKGROUND ART

The tetrapyrrole compounds such as porphyrin and chlorophyll are compounds important and useful as a variety of medical and pharmaceutical agents such as anticancer agents and, in addition thereto, they have also been used as food additives, and oxidation-reduction catalysts in the fields of electronics. Such a tetrapyrrole compound is in general prepared according to a chemical synthesis method. However, this chemical synthesis method suffers from such a problem that it requires the use of specific equipment (manufacturing equipment) and a specific catalyst and some of the chemical synthesis methods may adversely affect the environment due to the solvent used therein.

Over against this, there has been proposed a method for the preparation of a tetrapyrrole compound which makes use of a microorganism. For instance, there has been known a method in which a variant of the microorganism belonging to the genus *Plectonema* which is a kind of photosynthetic bacteria is cultivated and the resulting protochlorophyllide is then isolated and recovered from the culture medium (see, for instance, Patent Document 1 specified below). Moreover, there has been known a method in which photosynthetic bacteria are cultivated to thus isolate and recover the resulting tetrapyrrole compounds (see, for instance, Patent Documents 2 and 3 specified below). In addition, there has also been known a method in which a microorganism belonging to the genus *Arthrobacter* is cultivated in a culture medium containing a specific compound and then the resulting uroporphyrin is then collected from the culture medium (see, for instance, Patent Document 4 specified below).

Patent Document 1: Japanese Un-Examined Patent Publication Hei 5-91866;
Patent Document 2: Japanese Un-Examined Patent Publication Hei 5-244937;
Patent Document 3: Japanese Un-Examined Patent Publication 2000-23691;
Patent Document 4: Japanese Un-Examined Patent Publication Hei 5-38295.

DISCLOSURE OF THE INVENTION

Problems that the Invention is to Solve

When using the method disclosed in Patent Document 1, however, the resulting protochlorophyllide should be collected from the cultured bacterial cells and more specifically, it is necessary to destroy or crush the bacterial cells and subsequently separate and purify the product according to, for instance, the extraction technique. Moreover, when adopting one of the methods disclosed in Patent Documents 2 to 4, it is needed to incorporate, into the culture medium, 5-aminolevulinic acid as the precursor of a tetrapyrrole compound.

Accordingly, it is an object of the present invention to solve the foregoing problems associated with the foregoing conventional techniques and more particularly to provide a method for easily producing a tetrapyrrole compound while making use of bacterial cells of *Escherichia coli*, without using any precursor of the tetrapyrrole compound.

Means for the Solution of the Problems

The method for the production of a tetrapyrrole compound according to the present invention is characterized in that bacterial cells of *Escherichia coli*, which cannot express the gene ypjD (b2611) due to the variation or mutation thereof, are cultivated in a culture medium and that the resulting tetrapyrrole compound having a porphyrin ring structure is isolated and recovered from the culture medium.

The production method of the present invention is further characterized in that it comprises the steps of adding, to the culture medium, a metallic element capable of being converted into ions thereof in the foregoing culture medium or a metallic element-containing compound capable of being dissociated into its ions therein, as a raw material, and then collecting or isolating the resulting tetrapyrrole compound containing the metal.

The production method of the present invention is further characterized in that the foregoing tetrapyrrole compound is one which carries four methyl groups, and four ethyl ester groups or acetate groups (propionate groups) on the porphyrin ring of the compound.

In addition, the method for the production of a tetrapyrrole compound according to the present invention is likewise characterized in that it comprises the steps of cultivating bacterial cells of *Escherichia coli*, which cannot express the gene ypjD (b2611) due to the variation or mutation thereof, in a culture medium which comprises, as a raw material, element Mn capable of being converted into ions thereof in the culture medium or an Mn-containing compound capable of being dissociated into its ions therein and then collecting or isolating, from the culture medium, the resulting tetrapyrrole compound having a porphyrin ring structure in which Mn is coordinated at the center thereof.

The tetrapyrrole compound of the present invention is represented by the following formula:

$$[C_{36}H_{36}O_8N_4 \cdot Mn(III)]^+$$

Effect of the Invention

According to the present invention, a tetrapyrrole compound can be produced by cultivating bacterial cells of *Escherichia coli*, in particular, *Escherichia coli*, which cannot express the gene ypjD (b2611) due to the variation or mutation thereof in a culture medium and subsequently recovering or isolating the resulting tetrapyrrole compound having a porphyrin ring structure and accordingly, the present invention can easily provide a tetrapyrrole compound without using any precursor therefor.

BEST MODE FOR CARRYING OUT THE INVENTION

In the embodiment of the method for the production of a tetrapyrrole compound according to the present invention, the tetrapyrrole compound is produced by cultivating *Escherichia coli* preferably in an oligotrophic culture medium, isolating and recovering the intended tetrapyrrole compound from the oligotrophic culture medium to thus give the tetrapyrrole compound having a porphyrin ring structure. According to the present invention, the tetrapyrrole compound can be prepared by making *Escherichia coli* produce the same during the process for the cultivation and proliferation of the bacterial cells and subsequently recovering the tetrapyrrole compound secreted in the culture medium. It is preferred to use the oligotrophic culture medium as the culture medium, in order to prevent any influence of components such as natural substances present in the culture medium, which may be an obstacle to the isolation of the tetrapyrrole compound. As such oligotrophic culture mediums, there are preferably used, for instance, culture mediums each containing glucose or lactose, but the present invention is not restricted to the use thereof.

The *Escherichia coli* used in the present invention is preferably one which cannot express the gene ypjD (b2611) due to the variation or mutation thereof. Specific examples thereof include *Escherichia coli* cells derived from K12 strains and BL21 strains. For instance, preferably used herein are *Escherichia coli* cells derived from K12 strains, which cannot express the gene ypjD (b2611) due to the variation thereof. Examples of *Escherichia coli* strains which cannot express the gene ypjD (b2611) through the mutation include *Escherichia coli* strains wherein the transposon for the gene ypjD (b2611) is inserted into the gene of the strains. Such mutant strains are in such a condition that the function thereof for the expression of the gene ypjD (b2611) is partially or completely deleted. In this respect, the K12 strains are available from, for instance, National Bio-Resources, while the B21 strains are available from, for instance, TAKARA BIO. Moreover, the variant strains wherein the transposon for the gene ypjD (b2611) is inserted into the gene thereof include, for instance, JD23504 strains available from National Bio-Resources.

In this embodiment, *Escherichia coli* strains are first cultivated in an oligotrophic culture medium. In this respect, it is preferred that the *Escherichia coli* strains are pre-cultured in an appropriate culture medium other than the oligotrophic culture medium such as LB culture medium and that the pre-cultivated strains (or pre-cultivated products) are subsequently inoculated into an oligotrophic culture medium to thus carry out principal cultivation.

The conditions for growing *Escherichia coli* are not limited to any particular ones and the strains thereof can be cultivated under those currently used for the proliferation thereof. The same would be true for the following case, i.e., when *Escherichia coli* strains are first pre-cultured and then the principal cultivation thereof is carried out while replacing the culture medium with another one. For instance, the bacterial cells are pre-cultured in LB culture medium, at a temperature ranging from 15 to 40° C. for 6 to 24 hours and then the resulting cell suspension is subjected to the principal cultivation in an oligotrophic culture medium at a temperature ranging from 20 to 40° C. for 12 to 96 hours. Thus, the bacterial cells proliferate or grow in the culture medium and as a result, a culture (cultivated product) can be obtained, which has a color tone peculiar to the intended tetrapyrrole compound.

Then, the intended tetrapyrrole compound can be isolated from the foregoing cultivated product according to the method detailed below.

More specifically, the cultured product is centrifuged to give a supernatant followed by the filtration thereof, and then the tetrapyrrole compound is isolated from the filtrate through adsorption using, for instance, a column packed with an ion-exchange resin or a reversed phase column. For instance, the culture medium obtained after the cultivation of the bacterial cells is centrifuged to thus make the bacterial cells sediment or precipitate to thus give a supernatant containing culture (cultured product). Then the supernatant is filtered through a filter having a predetermined pore size (for instance, 0.22 μm) and then the resulting filtrate is loaded on the foregoing column packed with an ion-exchange resin to thus adsorb the intended products on the resin. Thereafter, the cultured product is eluted from the ion-exchange resin using, for instance, 20% acetonitrile-0.1% trifluoroacetic acid solution and then the resulting eluate is lyophilized. In this respect, it is also possible to use an eluting solution prepared by adding an aqueous solution of an acid or an alkali to an organic solvent in the foregoing elution step. According to this embodiment, one or at least two kinds of tetrapyrrole compounds are obtained and several milligrams to several ten-milligrams of tetrapyrrole compounds can be obtained from, for instance, 500 mL of the cell suspension.

The product isolated according to the foregoing procedures can be analyzed by, for instance, the NMR (Nuclear Magnetic Resonance) spectroscopic measurement to thus confirm whether or not the tetrapyrrole compounds are present in the product. In addition, when analyzing the product according to the spectrophotometric measurement, it would be found that the compounds are ones having an absorption peak within a wavelength region peculiar to the dyestuffs. In most of cases, those compounds are dyestuff compounds each showing a bilateral peak similar to those observed for chlorophyll, heme or phthalocyanine. Such dyestuff compounds are useful as photocatalysts or electron-transfer materials whose electrons are excited through the irradiation thereof with light rays. Moreover, they are involved in the reduction-oxidation (redox) reaction in an aqueous solution or through the cell membrane and accordingly, it would be believed that they can likewise function in a battery.

As has been discussed above in detail, according to the present invention, tetrapyrrole compounds and tetrapyrrole compounds containing a metal (complexes), for instance, porphyrins such as porphine, porphyrin and porphyrin complex can be produced using *Escherichia coli* and therefore, this method never requires the use of production devices and catalysts selected depending on the kinds of the intended compounds unlike the production thereof according to the chemical synthesis method, the former method does not require the use of any solvent and accordingly, it is only slightly apprehended that the method adversely affects the surrounding environment. In addition, it is not needed to add any precursor for the tetrapyrrole compound such as 5-aminolevulinic acid to the culture medium when cultivating *Escherichia coli*, and further it is sufficient to recover the tetrapyrrole compounds secreted in the culture medium and it is not necessary to collect the same from the bacterial cell. In other words, the method used in the present invention does not require the use of any particular compound and equipment for the cultivation of *Escherichia coli* and the recovery of the resulting tetrapyrrole compounds and accordingly, the method permits the easy production of the tetrapyrrole compounds. The tetrapyrrole compounds thus prepared can be used in a variety of industrial fields such as the medical care, food and electronics.

In this embodiment, the method of the present invention also comprises the steps of incorporating, into an oligotrophic culture medium, a metallic element capable of being converted into ions thereof in the foregoing culture medium or a metallic element-containing compound capable of being dissociated into its ions therein and then recovering a tetrapyrrole compound or a complex, which contains the metal. It is sufficient that such a metal is one capable of being converted into ions thereof. The compound containing such a metal is soluble in an acidic, alkaline or neutral aqueous solution. Examples of the foregoing metallic elements include at least one member selected from the group consisting of gold (Au), copper (Cu), potassium (K), manganese (Mn), zinc (Zn) and ruthenium (Ru). In addition, the metal may be added to the culture medium in the form of an inorganic metal compound or an organic metal compound. Examples of such inorganic metal compounds include sulfates, carbonates, nitrates, thiosulfates, oxides, nitrides or halides of the foregoing metals. Moreover, examples of the foregoing organic metal compounds are sodium gold thiomalate and zinc malate.

As has been described above, the incorporation, into the oligotrophic culture medium, of a metallic element capable of being converted into ions thereof in the culture medium or a metallic element-containing compound capable of being dissociated into its ions therein would permits the production of a tetrapyrrole compound or a complex having a color tone which may vary depending on the kind of the metal used. More specifically, if bacterial cells of Escherichia coli are cultivated in a culture medium, the metal element or metal compound incorporated into the cell bodies of Escherichia coli is converted into a compound tinged with a color tone originated from each metal incorporated into the bacterial cells due to the action of the gene of the Escherichia coli. Thereafter, the compound is released from the cells as a product and therefore, the secreted compound can be recovered from the culture medium to thus be able to obtain a compound useful as a dyestuff. To obtain a compound having a desired color tone, it is sufficient to properly select the metal depending on the desired color tone and this would surely eliminate the requirement for the development of novel methods for every intended compounds, which may vary between the color tones to be imparted to the compounds, unlike the production of such compounds according to the chemical synthesis methods. Incidentally, the resulting compounds may be applied to a variety of fields such as the fields of photocatalysts and optical butteries; and including the fields of, for instance, optical recording materials, information-recording materials, electron-transfer materials, semiconductor elements and electrodes.

The present invention is not restricted to the embodiments described above and includes various variations thereof without departing from the gist of the present invention.

The present invention will hereunder be described with reference to the following Examples.

Example 1

An insertion variant in which the transposon for the gene ypjD (b2611) had been inserted (JD23504 available from National Bio-Resources) were cultivated in 2 mL of LB culture medium (bacto-tryptone: 1%; bacto-yeast extract: 0.5%; NaCl: 0.5%) at 37° C. for 12 hours. There was added 1 mL of the resulting cell suspension to 500 mL of an aqueous solution prepared by adding 9 g of $KH_2PO_4$, 21 g of $K_2HPO_4$, 2 g of $(NH_4)_2SO_4$, 1 g of citric acid dihydrate, 3.6 g of glucose and 200 mg of $MgSO_4$ to 1 L of deionized water and the cells were subjected to principal cultivation at 37° C. for 24 hours.

The cultured liquid thus obtained was found to be colorless at the beginning of the principal cultivation, but the color thereof turned pink color after the elapse of 24 hours. This cultured liquid was treated using a centrifuge to thus precipitate the cells present therein and the resulting supernatant was filtered through a filter having a pore size of 0.22 μm. Then the resulting filtrate was passed through a column packed with an anion-exchange resin, subsequently the culture adsorbed on the resin was eluted from the same using a 20% acetonitrile-0.1% trifluoroacetic acid solution as an eluent and then the eluate was lyophilized. A product tinged with pink was thus recovered.

This product was subjected to a variety of instrumental analyses, such as those detailed below, and it was confirmed that the product was a tetrapyrrole compound having a structure as shown in FIG. 1. The symbols A to G appearing in FIG. 1 correspond to the marks specifying the corresponding $^{13}C$ NMR spectral peaks as shown in FIG. 4, these in the following figures are shown in the same way also. Moreover, the product was analyzed according to the NMR spectrometry and it was confirmed that a tetrapyrrole compound was certainly present in the product. Furthermore, the presence of potassium (K) was detected by the ICP (Inductively Coupled Plasma) mass spectrometric analysis and it was thus concluded that the compound was recovered as one ionically coupled with K or in the form of a complex with the same. In addition, the product was further subjected to the spectrophotometric analysis and as a result, it was confirmed that there was observed a bilateral peak including the Soret band peculiar to the porphyrin, as shown in FIG. 2. In FIG. 2, there are observed two peaks at wavelengths of 395 nm and 549 nm, respectively. This clearly indicates that the product is an organic dyestuff carrying free electrons capable of undergoing migration.

The tetrapyrrole compound prepared above was dissolved in different solvents (Sample 1 and Sample 2), the resulting samples were subjected to the two-dimensional NMR spectrometry (COSY, NOESY, HSQC, HMBC), followed by the analysis of the resulting spectra and the structural analysis of the compound.

Regarding the sample 1, it was dissolved in $CD_3OD$ and then the resulting solution was subjected to the NMR spectroscopic measurement under the following conditions:
Apparatus Used: INOVA500 Model (available from Variant Company);
Resonance Frequency: 499.8 MHz ($^1H$);
Standard: 3.31 ppm ($CD_2HOD$, $^1H$ NMR)
    49.421 ppm ($CD_3OD$, $^{13}C$ NMR);
Integration Number: $^1H$ NMR (16 times); $^{13}C$ NMR 53428 times); COSY (16 times) NOESY (8 times); HSQC (32 times); HMBC (128 times);
Other Condition: The mixing time of NOESY was set at a level of 400 msec.

In addition, as to the sample 2, it was dissolved in a 90:10:0.1 mixed $CD_3CN/D_2O/CD_3COOD$ solvent and then the resulting solution was subjected to the NMR spectroscopic measurement under the following conditions:
Apparatus Used: INOVA600 Model (available from Variant Company);
Resonance Frequency: 599.8 MHz ($^1H$);
Standard: 1.92 ppm ($CD_2HCN$, $^1H$ NMR)
    1.28 ppm ($CD_3CN$, $^{13}C$ NMR);
Integration Number: $^1H$ NMR (64 times); $^{13}C$ NMR 50000 times); COSY (16 times); NOESY (16 times); HSQC (32 times); HMBC (128 times);
Other Condition: The mixing time of NOESY was set at a level of 400 msec.
Structural Analysis of Sample 1:

The results of the $^1H$ NMR spectrometric analysis are plotted on FIG. 3 (solvent: $CD_3OD$). As a result, there were observed signals at about 10.0 to 10.5 ppm (d), around 4.3 ppm (f), around 3.6 ppm (g), and around 3.2 ppm (e), which were assumed to be ascribed to the intended component. The signals' intensity ratio was found to be about 1:2:3:2. The signals d to g are identical to those appearing on the other figures.

The results of the $^{13}C$ NMR spectrometric analysis are plotted on FIG. 4. It was thus assumed that the compound was an aromatic one because of the presence of signals B and C.

In this connection, the d signal observed in the $^1$H NMR spectrometric measurement is a characteristic signal which is not currently observed in the light of the magnitude of the chemical shift and it was assumed to be ascribed to the porphyrin skeleton, as a candidate, while taking into consideration the fact that the sample compound was an aromatic one. As will be described below, when analyzing the results (FIGS. 5 to 9) obtained by the two-dimensional NMR spectrometry while regarding the compound as a porphyrin, the results can be analyzed without any contradiction. Moreover, a compound having a structure similar to that estimated and depicted on FIG. 1 is reported in J. Org. Chem., 1999, Vol. 164, No. 21, pp. 7973-7982 and the magnitude of the chemical shift detected by the $^1$H NMR spectrometric measurement is well consistent with that disclosed in the article. Accordingly, it can reasonably be concluded that the compound has a porphyrin structure.

The analysis of the two-dimensional NMR spectrometric measurement will be described below in detail.

The results of the HSQC spectrometric analysis are shown in FIG. 5. The HSQC spectrometry is an analytical technique for the detection of $J^1_{CH}$. The results thus obtained are also depicted on FIG. 5. Regarding the proton signals, capital letters are ascribed to carbon atoms directly bonded.

The results of the COSY spectrometric analysis are shown in FIG. 6. The COSY spectrometry is an analytical technique for the detection of the spin coupling between $^1$H—$^1$H. As a result of the analysis, it was found that f and e caused a spin coupling and it was believed that this could be ascribed to —CH$_2$—CH$_2$—X at a high probability in consideration of the signal intensity ratio and the magnitudes of chemical shift for F and E. In this connection, X represents an unidentified component whose structure has not yet been elucidated.

The results of the HMBC spectrometric analysis are shown in FIG. 7. The HMBC spectrometry is an analytical technique for the detection of $J^n_{CH}$ (n=about 2 to 4), and this technique provides the heterogeneous nuclear remote coupling correlated spectra. The analysis of the spectrogram clearly indicates the presence of such correlations as (e, A), (e, B), (e, F), (g, B), (g, C), (f, A), (f, B), (f, C), (f, E). These correlations are never contradictory to the estimated structure as shown in FIG. 1.

The results of the NOESY spectrometric analysis are shown in FIGS. 8 and 9. The NOESY spectrometry is an analytical technique for the detection of the presence of magnetization-exchange and accordingly, this would be able to provide the information concerning the distance between nuclear spins on the basis of the magnetization shift due to the cross relaxation. The analysis of the spectrogram clearly indicates the presence of such NOE correlations as (g, e), (f, g), (f, e), (d, f), (d, e), (d, g) correlations. These NOE correlations clearly supported the reliability of the estimated structure as shown in FIG. 1.

Structural Analysis of Sample 2:

The results of the $^1$H NMR spectrometric analysis are plotted on FIG. 10 and the results of the $^{13}$C NMR spectrometric analysis are plotted on FIG. 11 (solvent: CD$_3$CN/D$_2$O/CD$_3$COOD=90:10:0.1). In FIG. 10, the signals enclosed in two squares are ascribed to impurities. As a result of the comparison with the spectra observed for the foregoing sample 1, it was assumed that the structures of the principal components were identical to one another. This was also supported by the analytical results of respective COSY, NOESY, HSQC and HMBC spectrograms.

FIG. 12 shows the enlarged NOESY spectrogram observed for the sample 2. There were observed the d proton splitted into four species and therefore, the numbers d1 to d4 were given to these species in the order from the low magnetic field side (in the ascending order). The NOE correlations are summarized as follows:

There were observed, for the both d1 and d4, the NOE correlations with the both methyl group and —CH$_2$—CH$_2$—X;

There was observed, for d2, the NOE correlation only with —CH$_2$—CH$_2$—X;

There was observed, for d3, the NOE correlation only with methyl group.

The arrangement of side chains as shown in FIG. 1 were elucidated on the basis of the fact that there was not observed any distinct NOE correlation between methyl groups or between —CH$_2$—CH$_2$—X groups in addition to the foregoing NOE correlations.

Regarding the numbering of the $^{13}$C signals and $^1$H signals, they were numbered in such a manner that the signals observed in an approximately identical region were numbered in a lump. This is because, the porphyrin skeleton has a repeated structure and therefore, the detailed attribution thereof was quite difficult. As to the number of repetition, there were observed four peaks to be attributable to methyl group (g) and accordingly, the number of repetition would be estimated to be 4.

According to the foregoing procedures, it could be confirmed that the compound had the structure as shown in FIG. 1 in the light of the analytical results of the sample 1 and 2. In this respect, however, it is sufficient that the number of respective side chains and more specifically methyl groups and —CH$_2$—CH$_2$—X groups are four in total, the position of each side chain attached may be either one of the 8 sites as shown in FIG. 1 and this is not in contradiction to the foregoing data. Accordingly, the position thereof is not restricted to those specified in FIG. 1.

Then the portion corresponding to X in the group: —CH$_2$—CH$_2$—X was investigated.

The product obtained according to the foregoing procedures was subjected to the following analysis:

(1) Qualitative Analysis According to Pyrolytic GC/MS:

To remove TFA or the like, the sample was heated at 280° C. for 10 minutes in a heating furnace, then thermally decomposed at 600° C. and the decomposition products were separated and analyzed using the gas chromatograph/mass spectrograph (hereunder referred to as "GC/MS") as detailed below.

Name of the Device:

A device available from Agilent Technologies under the trade name of HP5973: Type equipped with a mass-selective detector; and HP6890 Type: Gas Chromatograph;

A device available from FRONTIER LAB under the trade name of PY-2020iD: Heating Furnace type Decomposition Device.

Sample to be Analyzed: A solution (0.5 mL) obtained by adding 1 mL of AcCN to 2 mg of each sample was poured into a sample cup and then AcCN was removed by purging the cup with nitrogen gas.

(2) Analysis with Electrospray Ionization-Mass Spectrograph:

To examine the molecular weight of the components present in the solution, each sample was analyzed using the Electrospray Ionization-Mass Spectrograph (hereunder referred to as "ESI-MS") as detailed below:

Name of the Device: Qstar available from Applied Biosystems;

Solvent Introduced AcCN/0.05% aqueous formic acid solution (50/50);

Method of Introduction: The solution to be analyzed was directly introduced using a 30 μL loop.

Mode of Measurement: Positive Mode;
Solution to be Analyzed: A small amount of a solution obtained by adding 1 mL of AcCN to 2 mg of each sample was dispensed in a vial and then diluted to about 100 ppm with the introduction solvent.

The results obtained in the foregoing GC/MS analysis indicated that carbon dioxide was detected in the sample. In addition, As seen from the results (see FIG. 14) obtained in the foregoing ESI-MS analysis, fragment ions having a molecular weight of 59 (4 peaks) were detected and accordingly, it was confirmed that the fragment comprised an ethyl ester group or acetic acid group (a propionic acid group).

Moreover, the foregoing product was analyzed by the pyrolytic GC-MS technique and as a result, the main component thereof was found to be a pyrrole compound as shown in FIG. 15. This fact could be confirmed by comparing the mass spectral data of each component with the data base and as a result, it could be confirmed that the product had a pyrrole ring structure in the molecule. In addition, in respect of the detailed molecular weight, it was detected as an ion formed through the addition of a hydrogen ion to the product as shown in FIG. 13 and thus the molecular weight thereof was found to be 654.2682 (=655.2760−1.0078). From the foregoing, it was confirmed that the product was a porphyrin compound carrying, on the side chains, 4 ethyl ester groups or acetic acid groups (propionic acid groups) and 4 methyl groups, having a molecular weight of 654 and having the following molecular formula: $C_{36}H_{38}O_8N_4$.

Example 2

Bacterial cells, more specifically *Escherichia coli* strains wherein the transposon for the gene ypjD (b2611) had been inserted into the gene of the strains (a transposon-inserted variant: JD23504, available from National Bio-Resources) were subjected to a preculture in 2 mL of LB culture medium (including Bacto-tryptone: 1%; Bacto-yeast extract: 0.5%; and NaCl: 0.5%) at a temperature of 37° C. over 12 hours. The resulting cell suspension (1 mL) was added to an aqueous solution obtained by dissolving, in one liter of deionized water, 20 mg of $MnCl_2$, 1 g of citric acid dihydrate, 3.6 g of glucose, and 100 mg of $MgSO_4$, and then the bacterial cells were subjected to the principal cultivation at a temperature of 37° C. over 24 hours.

The culture medium (culture solution) was found to be colorless at the initiation of the principal cultivation, but the culture medium turned reddish brown, after the elapse of 24 hours. The culture medium was subjected to a treatment in a centrifuge to thus precipitate the bacterial cells and the resulting supernatant was filtered through a filter having a pore size of 0.22 μm. Then the filtrate was passed through a column packed with an anion-exchange resin, the cultured materials adsorbed on the resin were eluted using an eluting solution consisting of a 20% acetonitrile-0.1% trifluoroacetic acid aqueous solution and then the eluate was freeze-dried. Thus, there was recovered a product tinged with reddish brown.

In addition, the foregoing product was analyzed by the pyrolytic GC-MS technique and as a result, the main component thereof was found to be a pyrrole compound as shown in FIG. 16. This fact could be confirmed by comparing the mass spectral data of each component with those listed in the data base and as a result, it could be confirmed that the product had a pyrrole ring structure in the molecule. Moreover, the product was further subjected to the ESI-MS mass spectrometric analysis and it was found that this compound had a molecular weight of 707 (see the data plotted on FIG. 17), that four fragments each having a molecular weight of 59 were in order detected in the MS/MS measurement (see the data plotted on FIG. 18), that the presence of $CO_2$ was detected in the analysis according to the pyrolytic GC-MS technique, as in the case of Example 1, and that the compound included 4 ethyl ester groups or acetate groups (propionate groups) in all. FIG. 19 shows the absorption spectrogram observed for the same product having a color tone tinged with an orange color.

Moreover, it was found, from the results of the XPS elemental analysis (see the data plotted on FIG. 20), that the compound contained Mn atom. From the results obtained through the detailed mass spectrometric analysis discussed above, it was confirmed that the product of this Example is a compound having the structure of a porphyrin compound in common with the product of Example 1 and it was also proved that the product of this Example is that prepared in Example 1 from which two central hydrogen atoms are eliminated and in which a trivalent Mn ion is coordinated at the center thereof, on the basis of the detailed examination of the difference in the mass between the mass of the product of Example 1 (having a molecular weight of 654.2682) and the mass of the product of this Example (as will be seen from the data plotted on FIG. 17, the product has a molecular weight of 707.1905) (more specifically, 654.2682 (molecular weight of the product of Example 1)−1.0078×2 (atomic weight of H×2)+54.9380 (atomic weight of Mn)=707.1906).

From the foregoing, it was thus confirmed that the resulting product is a porphyrin compound which carries four —$CH_2$—$CH_2$—COOH groups (propionate groups) and four methyl groups on the side chains, which has a molecular weight (the molecular weight thereof in the ionized state) of 707 and which is represented by the formula (In its ionized form) of $[C_{36}H_{36}O_8N_4.Mn(III)]^+$.

Example 3

Bacterial cells, more specifically *Escherichia coli* strains wherein the transposon for the gene ypjD (b2611) had been inserted into the gene of the strains (a transposon-inserted variant: JD23504, available from National Bio-Resources) were subjected to a preculture in 2 mL of LB culture medium (including Bacto-tryptone: 1%; Bacto-yeast extract: 0.5%; and NaCl: 0.5%) at a temperature of 37° C. over 12 hours. The resulting cell suspension (1 mL) was added to an aqueous solution obtained by dissolving, in one liter of deionized water, 25 mg of sodium gold thiomalate, 1 g of citric acid dihydrate, 3.6 g of glucose, and 100 mg of $MgSO_4$, and then the bacterial cells were subjected to the principal cultivation at a temperature of 37° C. over 24 hours.

The culture medium was found to be colorless at the beginning of the principal cultivation, but the culture medium turned yellow, after the elapse of 24 hours. The culture medium was subjected to a treatment in a centrifuge to thus precipitate the bacterial cells and the resulting supernatant was filtered through a filter having a pore size of 0.22 μm. Then the filtrate was passed through a column packed with an anion-exchange resin, the cultured materials adsorbed on the resin were eluted using an eluting solution consisting of a 20% acetonitrile-0.1% trifluoroacetic acid aqueous solution and then the eluate was freeze-dried. Thus, there was recovered a product tinged with yellow. The resulting product was subjected to the ICP mass spectrometric analysis, and as a result, it was found that the product contains a metallic gold (Au). Furthermore, this product was likewise analyzed according to the pyrolytic GC-MS technique, and as a result, it was confirmed that the product mainly comprises a pyrrole compound and that the compound comprises a pyrrole ring structure in the molecule.

Example 4

Bacterial cells, more specifically *Escherichia coli* strains wherein the transposon for the gene ypjD (b2611) had been inserted into the gene of the strains (a transposon-inserted variant: JD23504, available from National Bio-Resources) were subjected to a preculture in 2 mL of LB culture medium (including Bacto-tryptone: 1%; Bacto-yeast extract: 0.5%; and NaCl: 0.5%) at a temperature of 37° C. over 12 hours. The resulting cell suspension (1 mL) was added to an aqueous solution obtained by dissolving, in one liter of deionized water, 20 mg of $CuCl_2$, 1 g of citric acid dihydrate, 3.6 g of glucose, and 100 mg of $MgSO_4$, and then the bacterial cells were subjected to the principal cultivation at a temperature of 37° C. over 24 hours.

The culture medium was found to be colorless at the beginning of the principal cultivation, but the culture medium turned bluish green, after the elapse of 24 hours. The culture medium was subjected to a treatment in a centrifuge to thus precipitate the bacterial cells and the resulting supernatant was filtered through a filter having a pore size of 0.22 μm. Then the filtrate was passed through a column packed with an anion-exchange resin, the cultured materials adsorbed on the resin were eluted using an eluting solution consisting of a 20% acetonitrile-0.1% trifluoroacetic acid aqueous solution and then the eluate was freeze-dried. Thus, there was recovered a product tinged with green. The resulting product was subjected to the ICP mass spectrometric analysis and as a result, it was found that the product contains a metallic copper (Cu). Furthermore, this product was likewise analyzed according to the pyrolytic GC-MS technique and as a result, it was confirmed that the product mainly comprises a pyrrole compound and that the compound comprises a pyrrole ring structure in the molecule.

Example 5

Bacterial cells, more specifically *Escherichia coli* strains wherein the transposon for the gene ypjD (b2611) had been inserted into the gene of the strains (a transposon-inserted variant: JD23504, available from National Bio-Resources) were subjected to a preculture in 2 mL of LB culture medium (including Bacto-tryptone: 1%; Bacto-yeast extract: 0.5%; and NaCl: 0.5%) at a temperature of 37° C. over 12 hours. The resulting cell suspension (1 mL) was added to an aqueous solution obtained by dissolving, in one liter of deionized water, 17 mg of $ZnCl_2$, 1 g of citric acid dihydrate, 3.6 g of glucose and 100 mg of $MgSO_4$, and then the bacterial cells were subjected to the principal cultivation at a temperature of 37° C. over 24 hours.

The culture medium was found to be colorless at the beginning of the principal cultivation, but the culture medium turned green tinged with red, after the elapse of 24 hours. The resulting culture, medium was treated according to the same procedures used in Example 1 and as a result, there was recovered a product tinged with green.

This product obtained through the foregoing cultivation, tinged with green color tone was analyzed by the mass spectrometry according to the TOF-MS technique. As a result, the product was found to be a mixture whose molecular weight falls within the range of from 307 to 1294 as will be seen from the data plotted on FIG. 21. In addition, the product was likewise analyzed by the ICP mass spectrometry and as a result, it was thus confirmed that the product contains elemental zinc. As will be seen from the absorption spectrophotometric curve given in FIG. 22, the product shows two peaks at wavelengths of 372 nm and 445 nm, respectively. Furthermore, the product was also analyzed by the pyrolytic GC-MS technique and as a result, it was confirmed that the product mainly comprises a pyrrole compound and that the pyrrole compound comprises a pyrrole ring structure in the molecule.

Example 6

Bacterial cells, more specifically *Escherichia coli* strains wherein the transposon for the gene ypjD (b2611) had been inserted into the gene of the strains (a transposon-inserted variant: JD23504, available from National Bio-Resources) were subjected to a preculture in 2 mL of LB culture medium (including Bacto-tryptone: 1%; Bacto-yeast extract: 0.5%; and NaCl: 0.5%) at a temperature of 37° C. over 12 hours. The resulting cell suspension (1 mL) was added to an aqueous solution obtained by dissolving, in one liter of deionized water, 10 mg of $RuCl_3$, 1 g of citric acid dihydrate, 3.6 g of glucose, and 100 mg of $MgSO_4$, and then the bacterial cells were subjected to the principal cultivation at a temperature of 37° C. over 24 hours.

The culture medium or cultured liquid was found to be colorless at the beginning of the principal cultivation, but the culture medium turned bluish green, after the elapse of 24 hours. The cultured liquid was subjected to a treatment in a centrifuge to thus precipitate the bacterial cells and the resulting supernatant was filtered through a filter having a pore size of 0.22 μm. Then the filtrate was passed through a column packed with an anion-exchange resin, the cultured materials adsorbed on the resin were eluted using an eluting solution consisting of a 20% acetonitrile-0.1% trifluoroacetic acid aqueous solution and then the eluate was freeze-dried. Thus, there was recovered a product tinged with green. The resulting product was subjected to the ICP mass spectrometric analysis and as a result, it was found that the product contains a metallic ruthenium (Ru). Furthermore, this product was likewise analyzed according to the pyrolytic GC-MS technique and as a result, it was confirmed that the product mainly comprises a pyrrole compound and that the pyrrole compound comprises a pyrrole ring structure in the molecule.

INDUSTRIAL APPLICABILITY

The tetrapyrrole compound prepared according to the present invention may be applied to or used in a variety of fields such as the fields of photocatalysts and optical butteries; and including the fields of, for instance, optical recording materials, information-recording materials, electron-transfer materials, semiconductor elements and electrodes.

Figure 1:
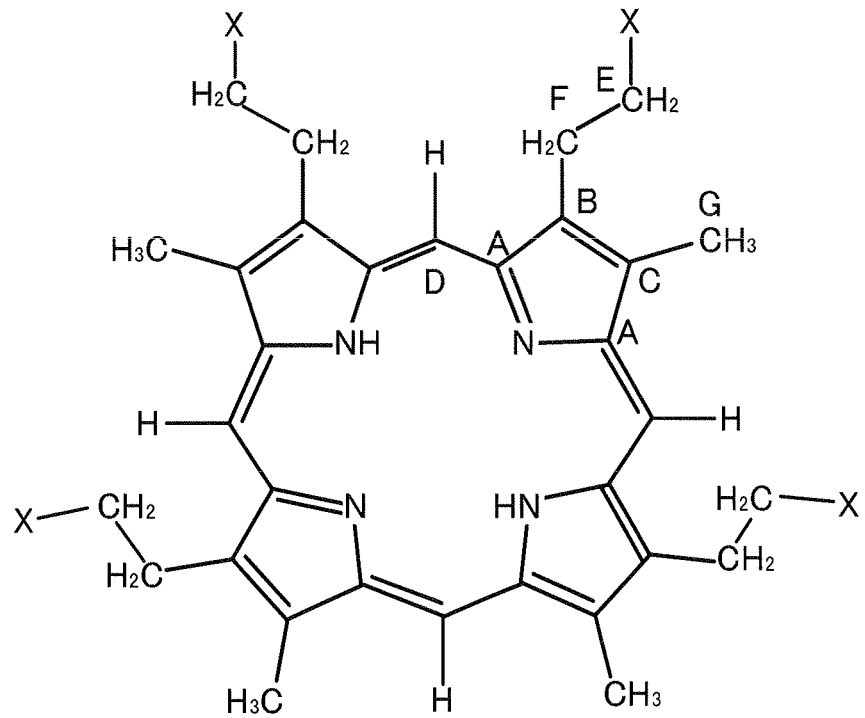
FIG. 1 shows the spectra as the result of the analysis of the mass spectrometry according to the TOF-MS technique, which was observed for the product produced in Example 1.
Figure 2:
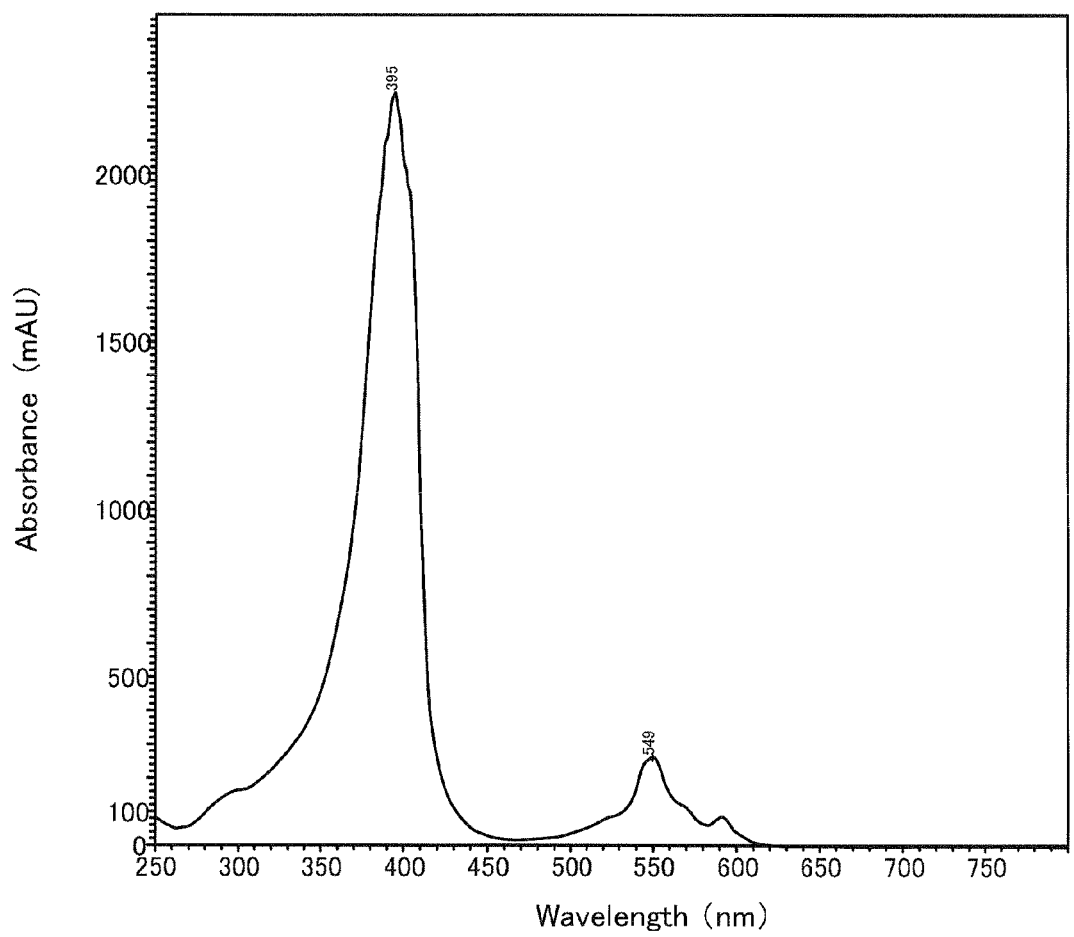
FIG. 2 shows the structural formula of the product produced in Example 1.
Figure 3:
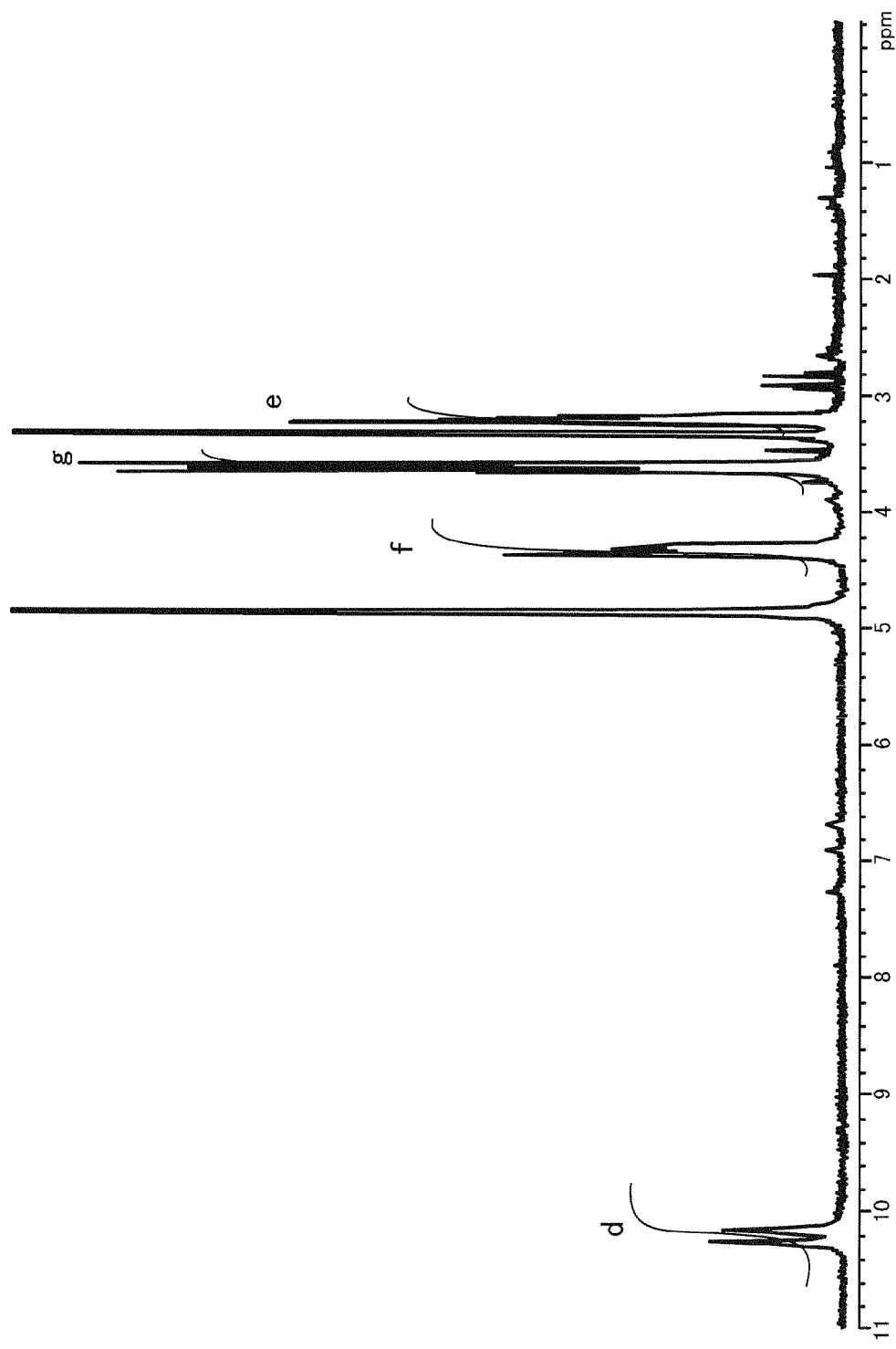
FIG. 3 shows the $^1H$ NMR spectra observed for Sample 1 prepared in Example 1.
Figure 4:
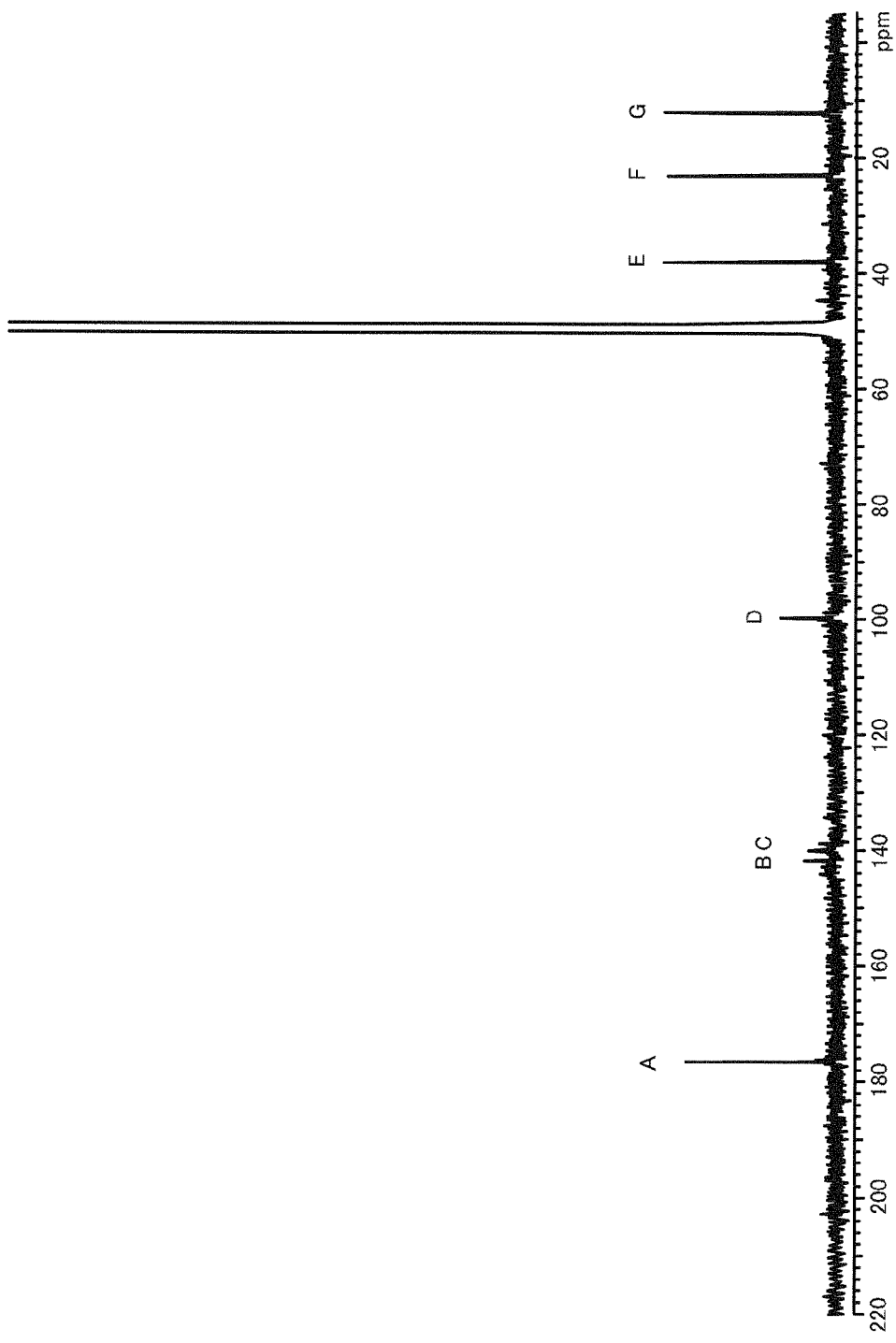
FIG. 4 shows the $^{13}C$ NMR spectra observed for Sample 1 prepared in Example 1.
Figure 5:
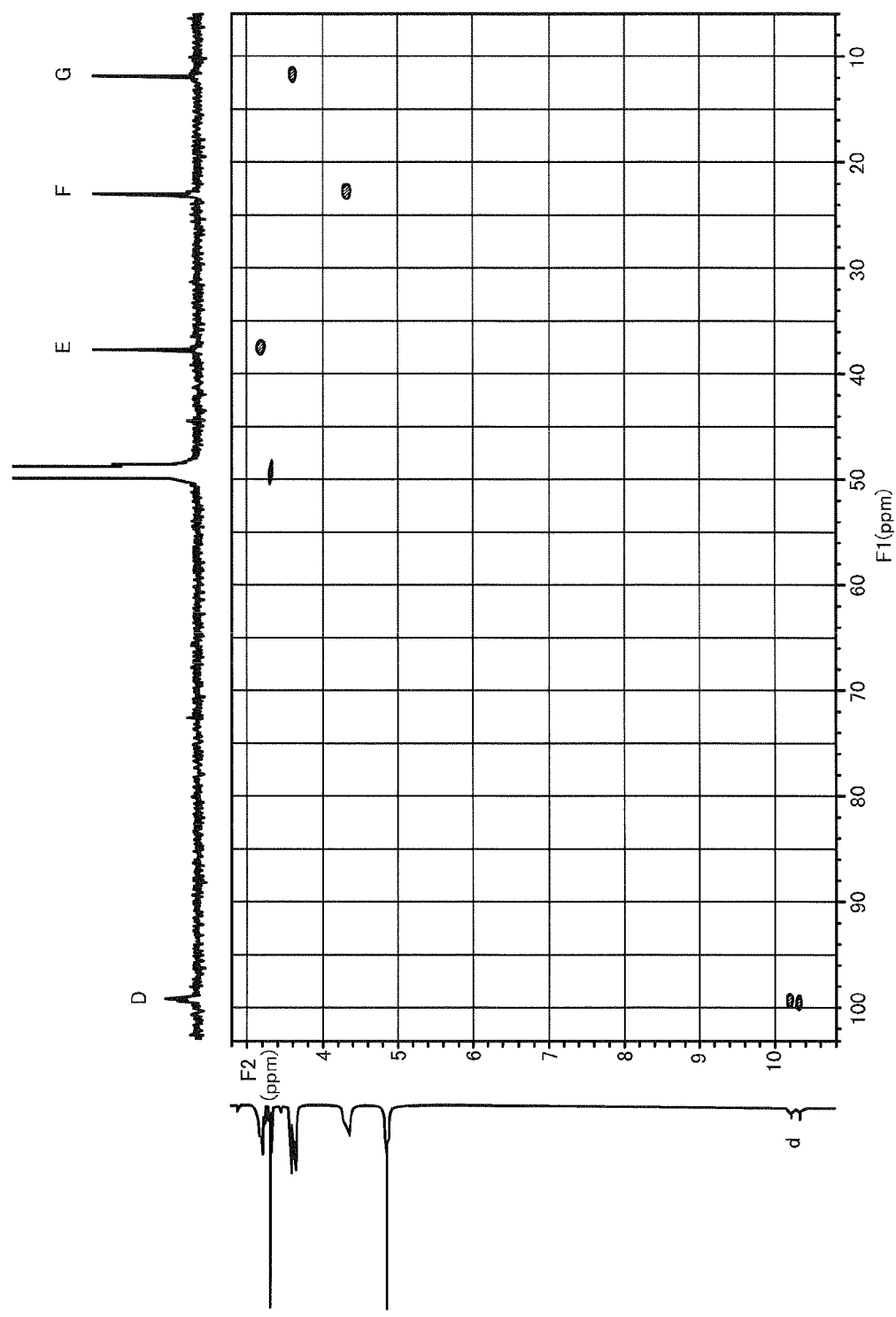
FIG. 5 shows the HSQC spectra observed for Sample 1 prepared in Example 1.
Figure 6:
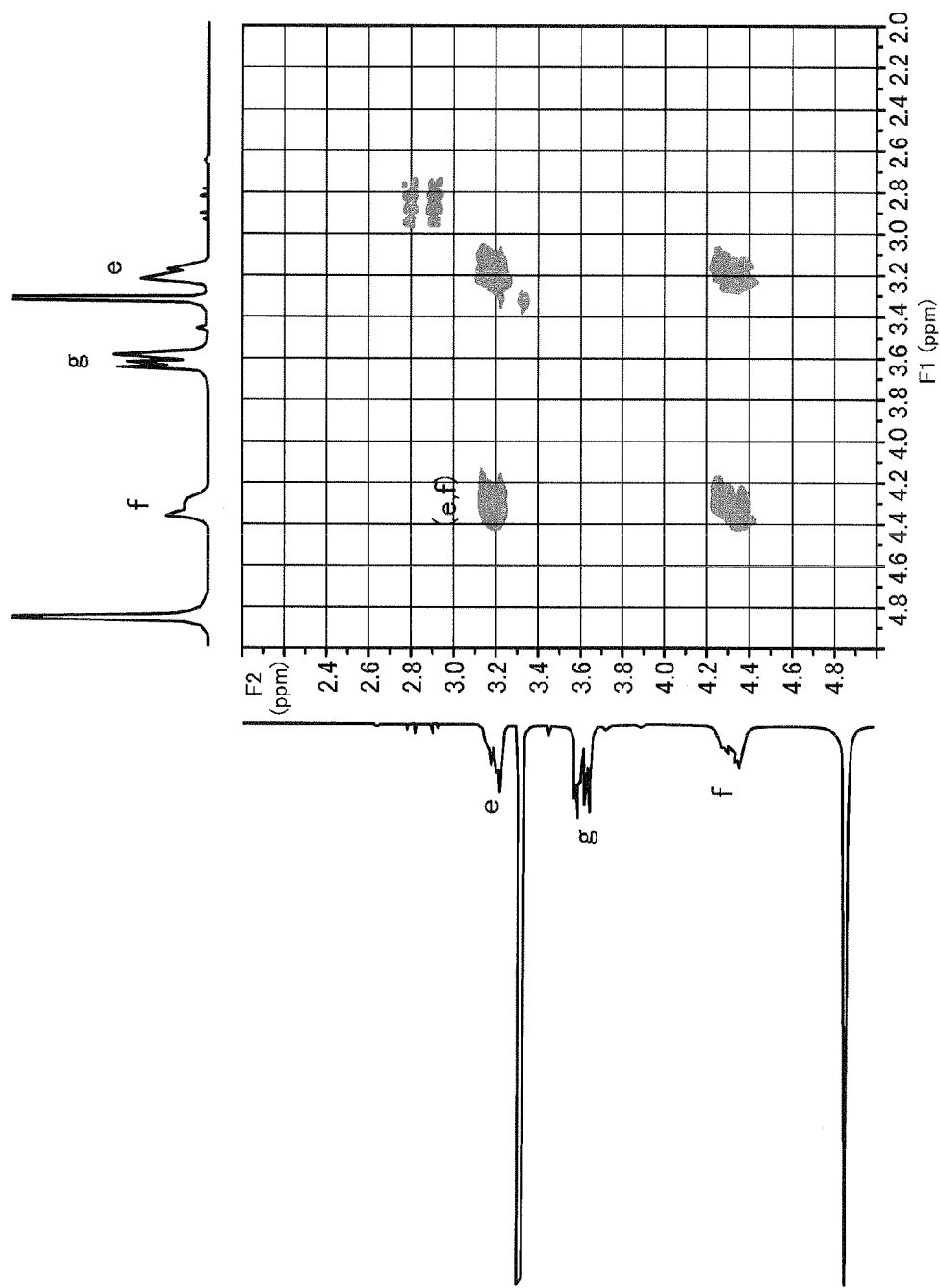
FIG. 6 shows the COSY spectra observed for Sample 1 prepared in Example 1.
Figure 7:
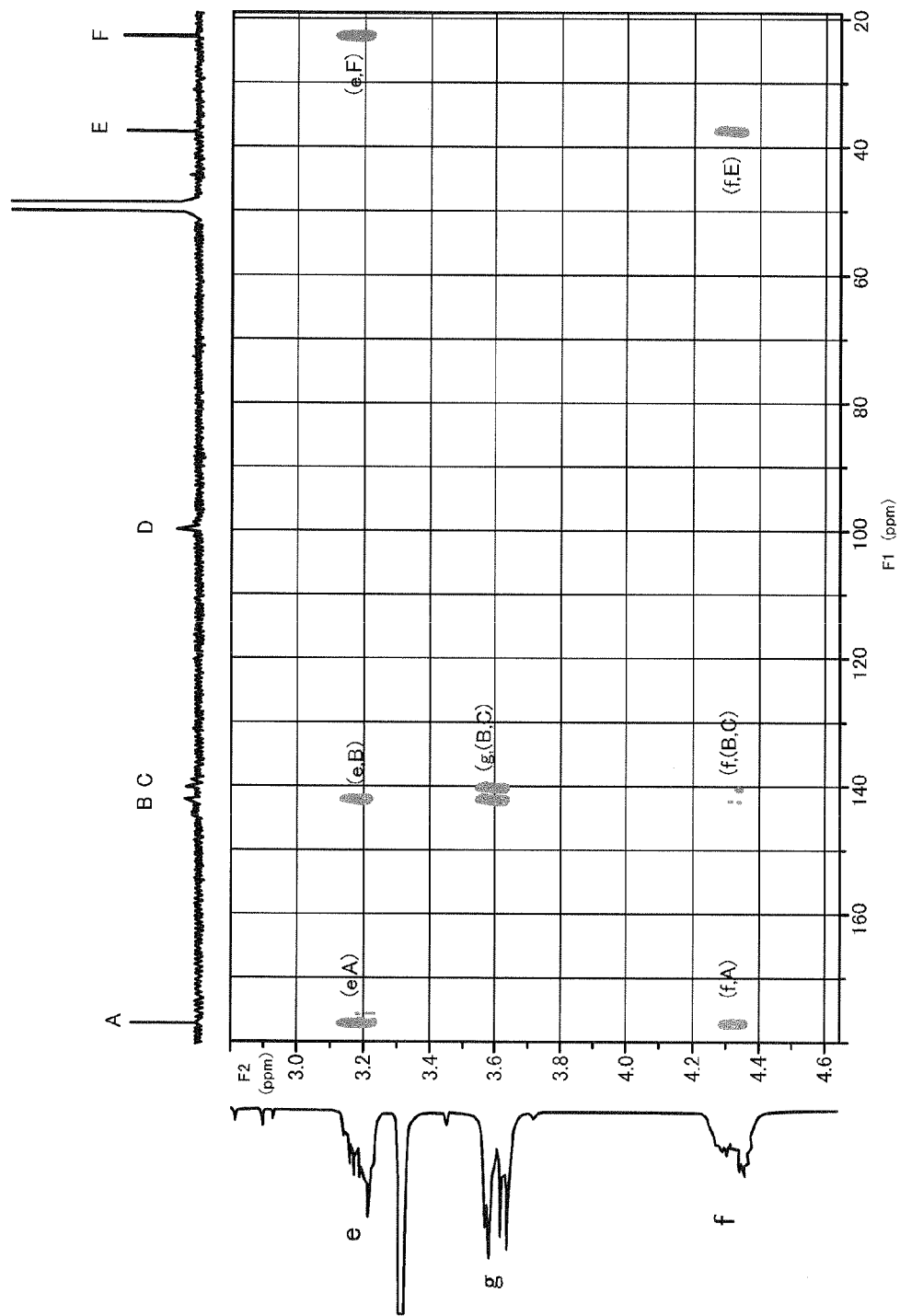
FIG. 7 shows the HMBC spectra observed for Sample 1 prepared in Example 1.
Figure 8:
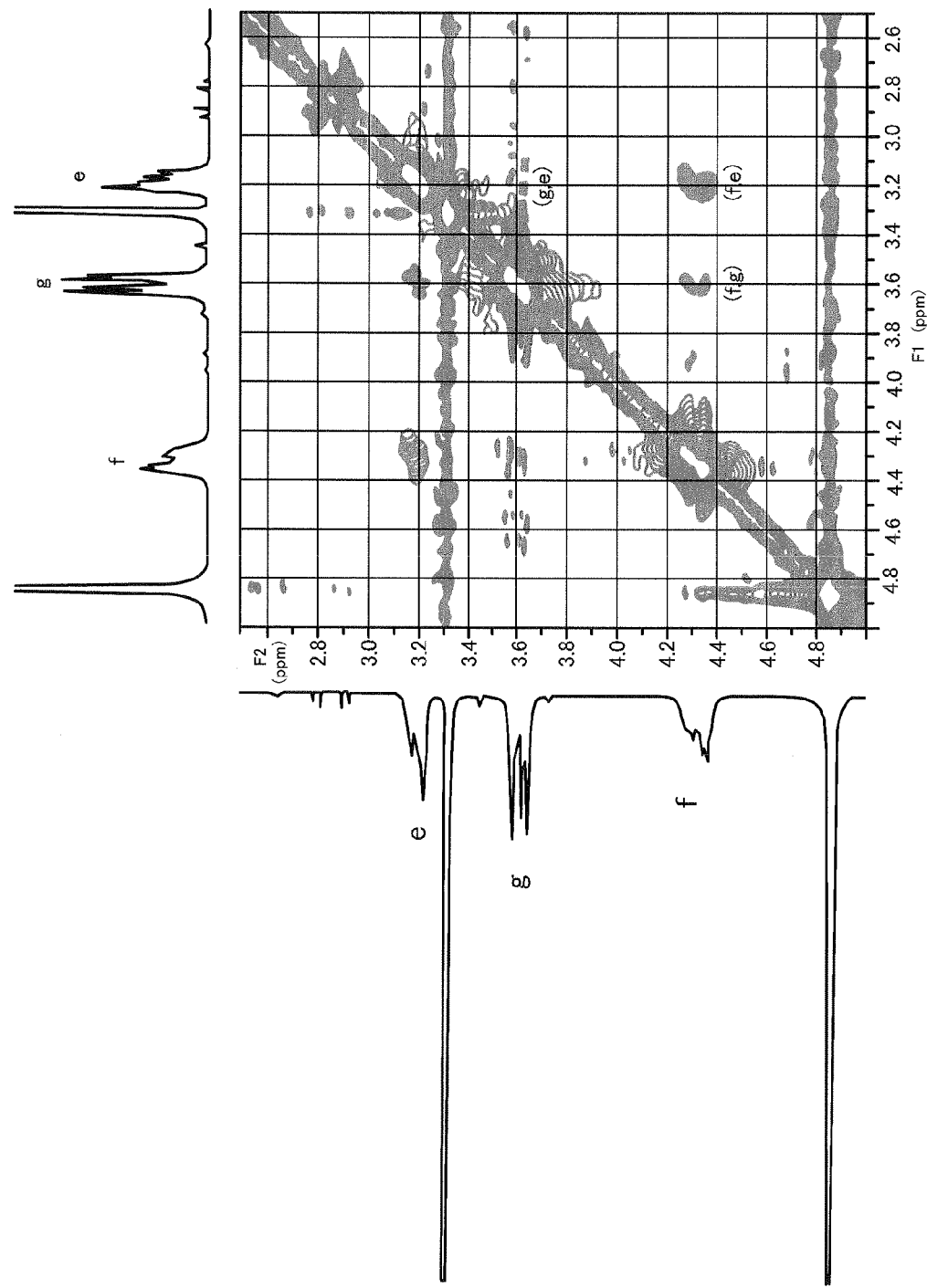
FIG. 8 shows the NOESY spectra observed for Sample 1 prepared in Example 1.
Figure 9:
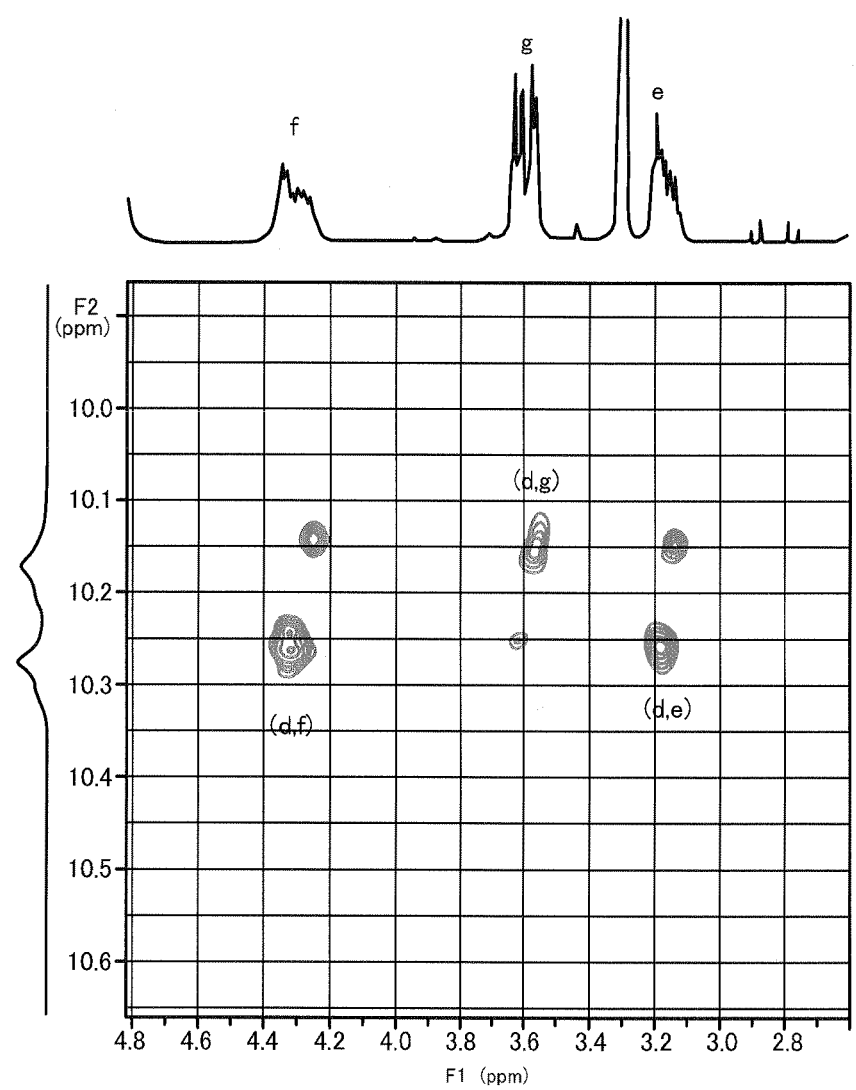
FIG. 9 shows the NOESY spectra observed for Sample 1 prepared in Example 1.
Figure 10:
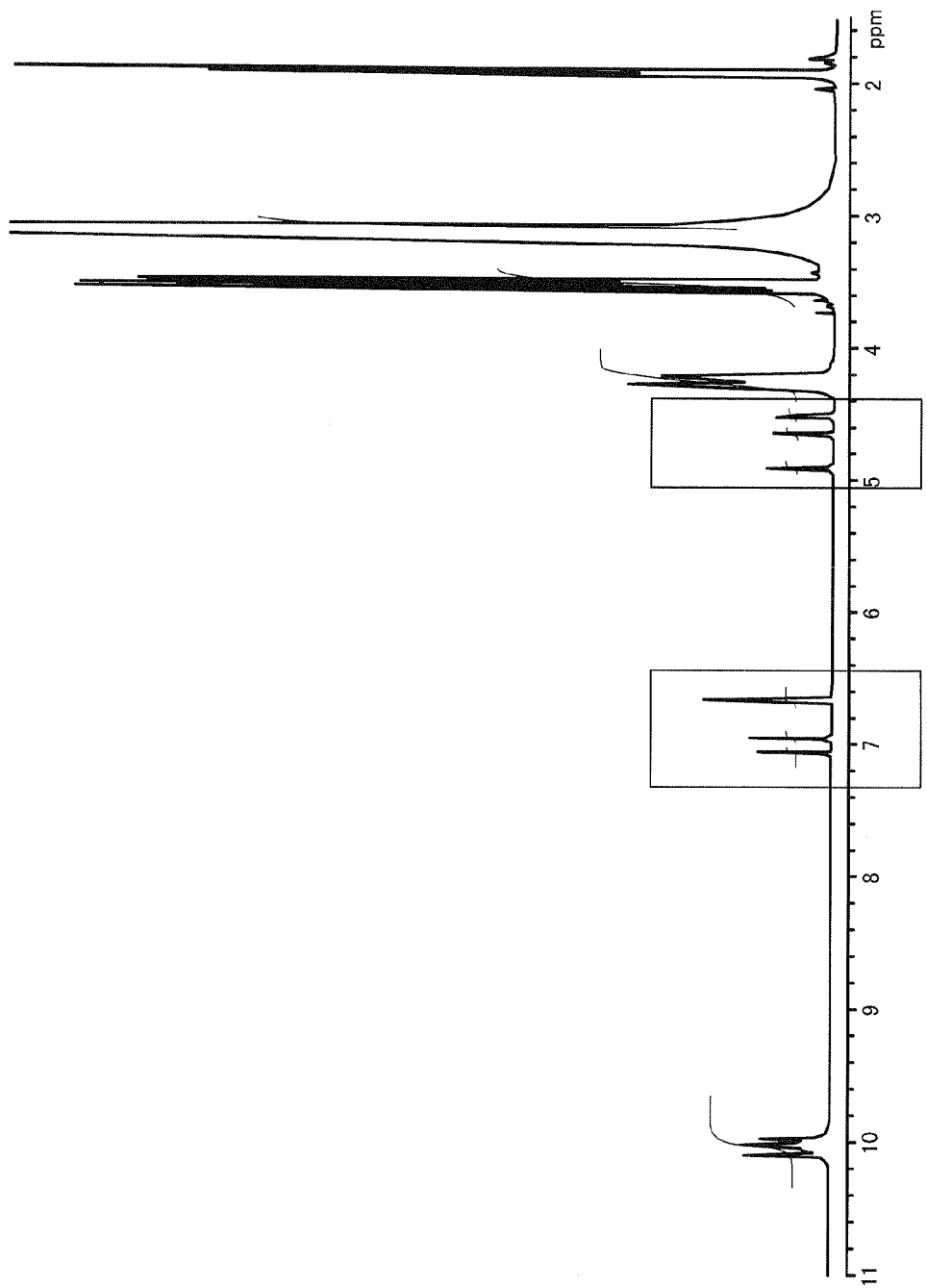
FIG. 10 shows the $^1$H NMR spectra observed for Sample 2 prepared in Example 1.
Figure 11:
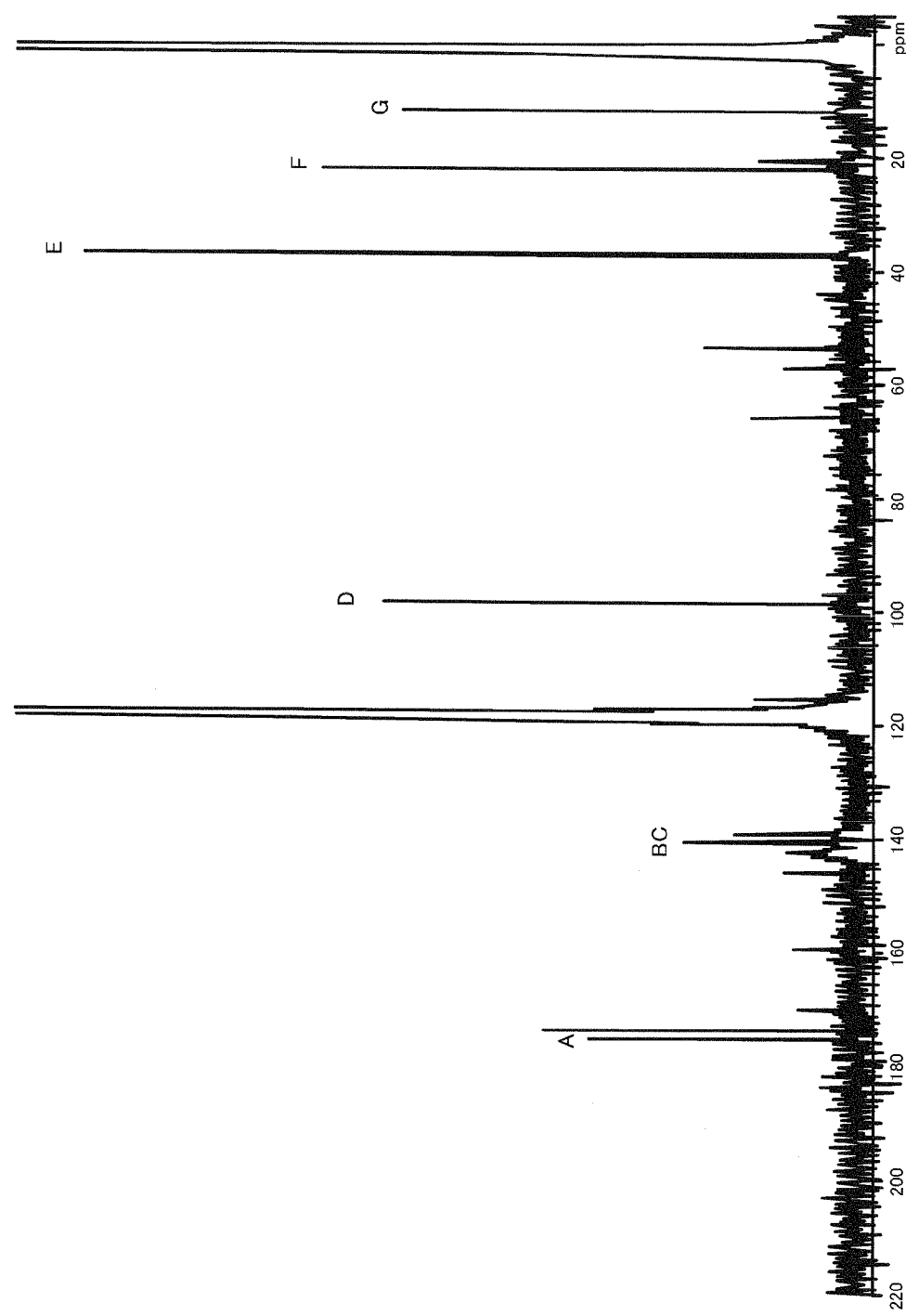
FIG. 11 shows the $^{13}$C NMR spectra observed for Sample 2 prepared in Example 1.
Figure 12:
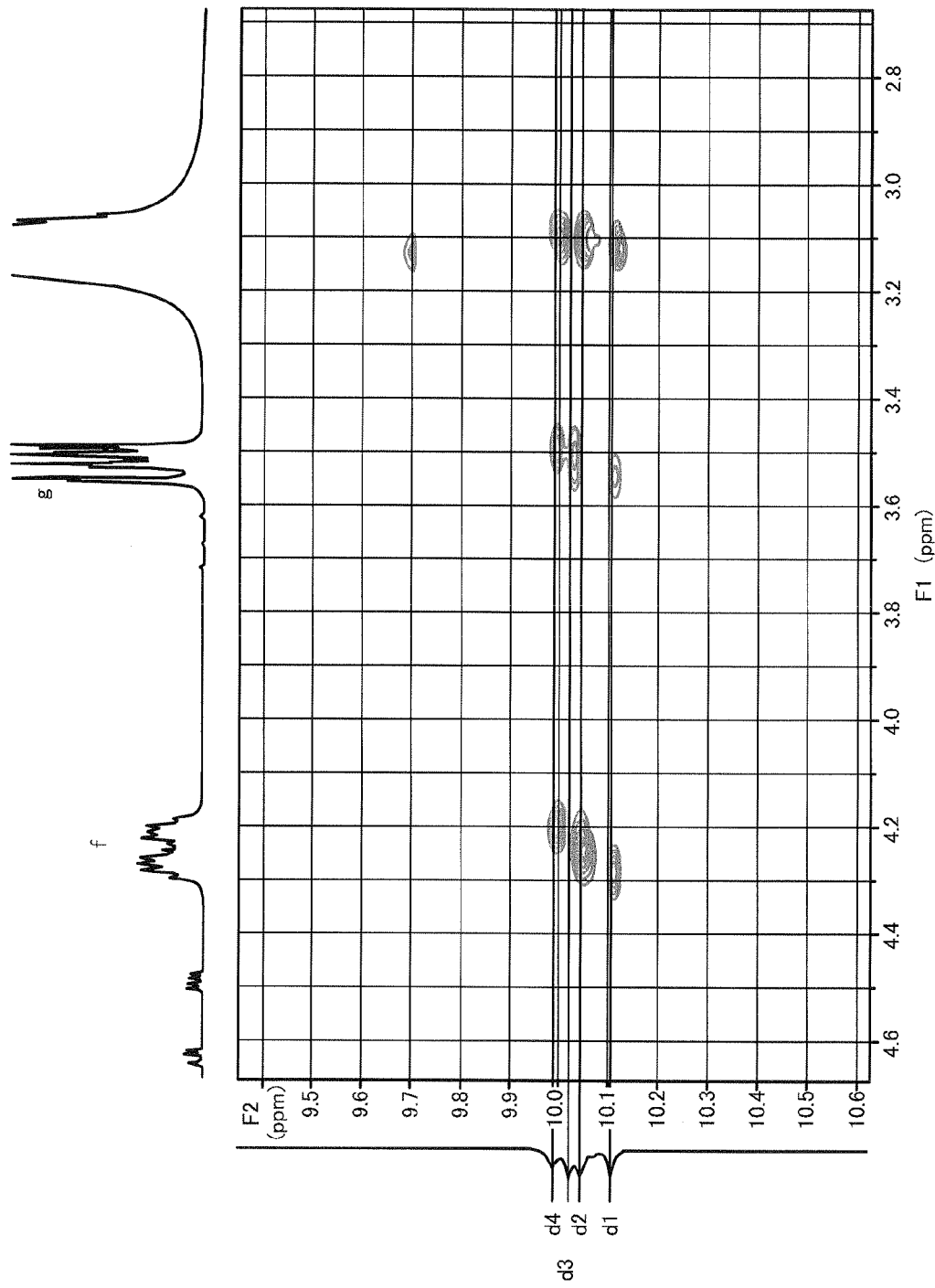
FIG. 12 shows an enlarged NOESY spectra observed for Sample 2 prepared in Example 1.
Figure 13:
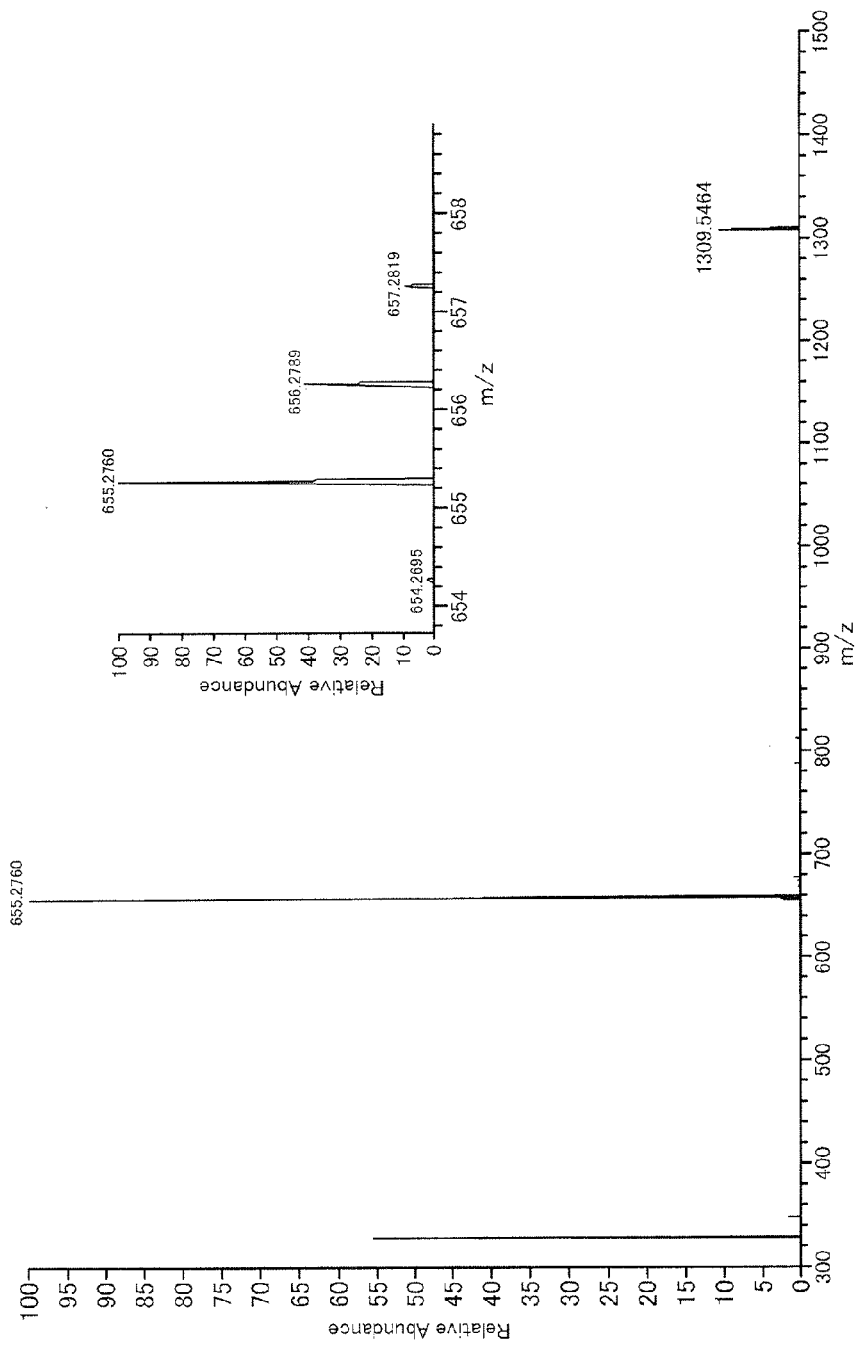
FIG. 13 shows the spectra illustrating the relative abundance observed for Sample 2 prepared in Example 1.
Figure 14:
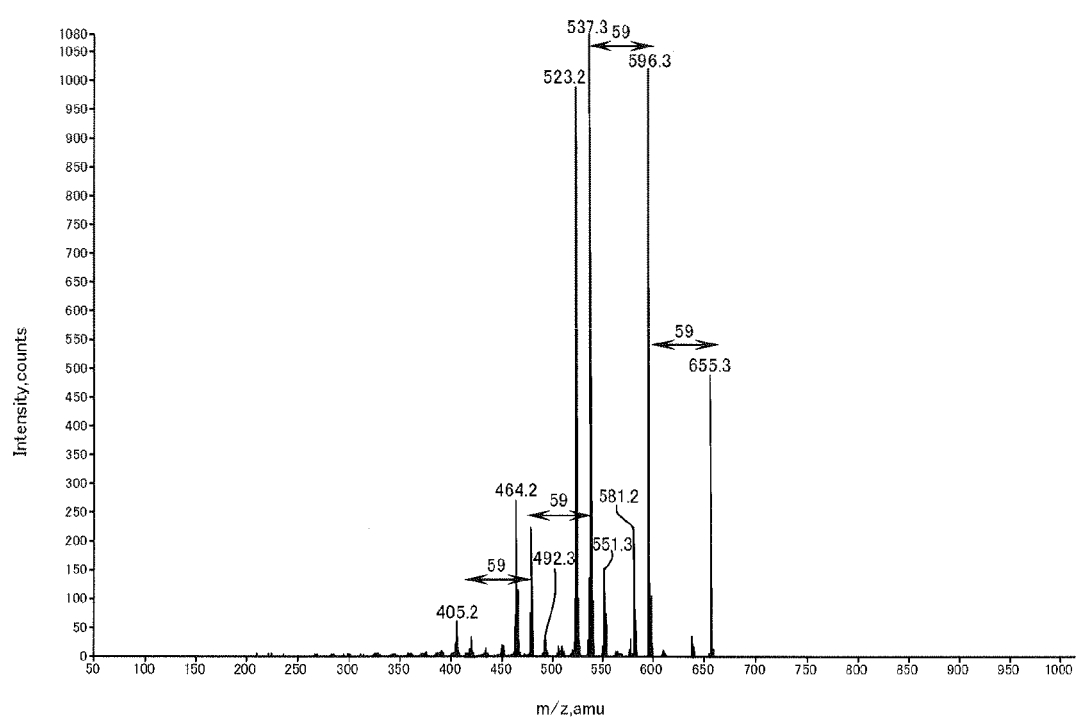
FIG. 14 shows the results of the analysis carried out according to the ESI-MS.
Figure 15:
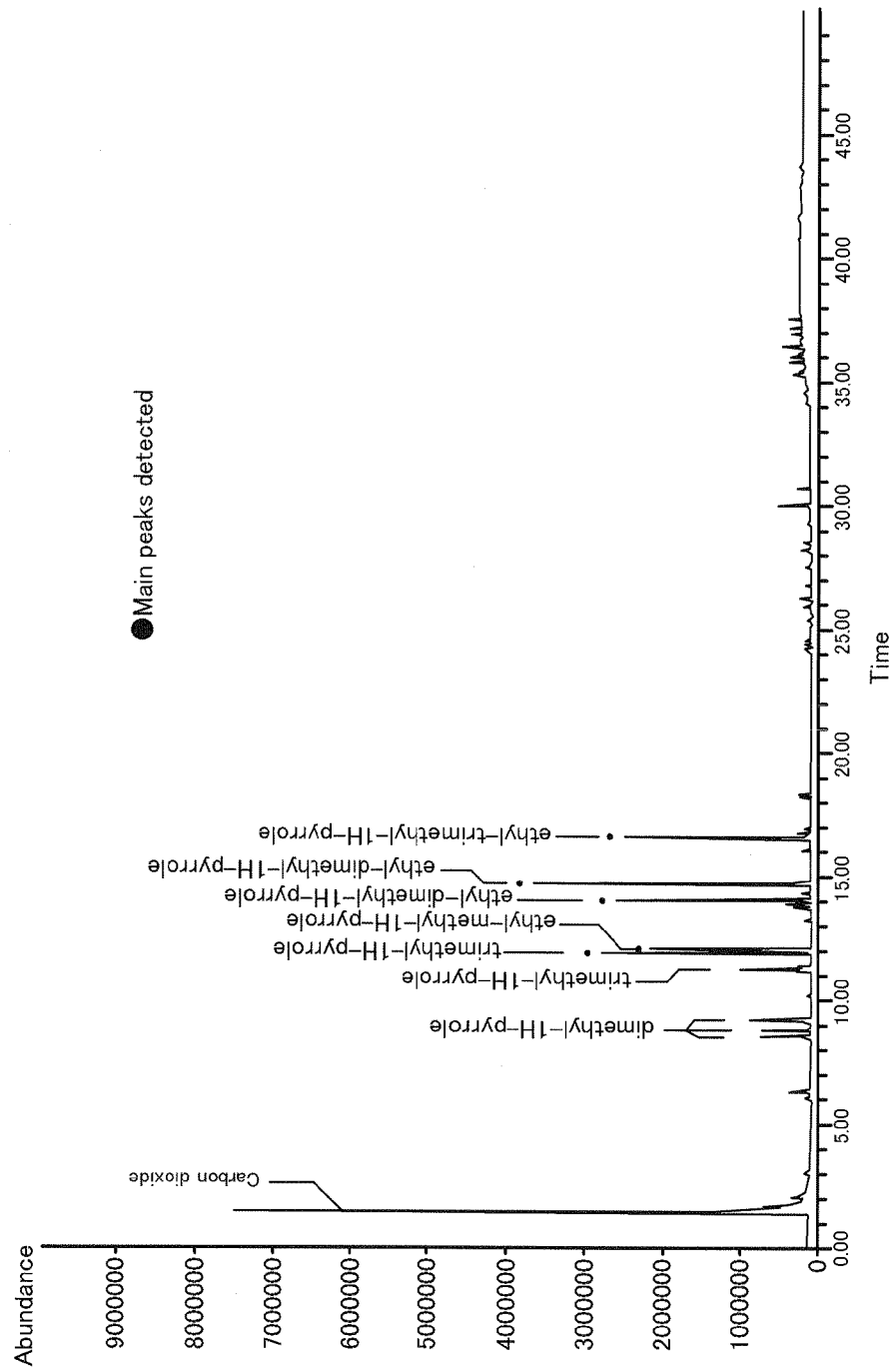
FIG. 15 shows the results of the analysis of the product prepared in Example 1, which is carried out according to the pyrolysis GC-MS.
Figure 16:
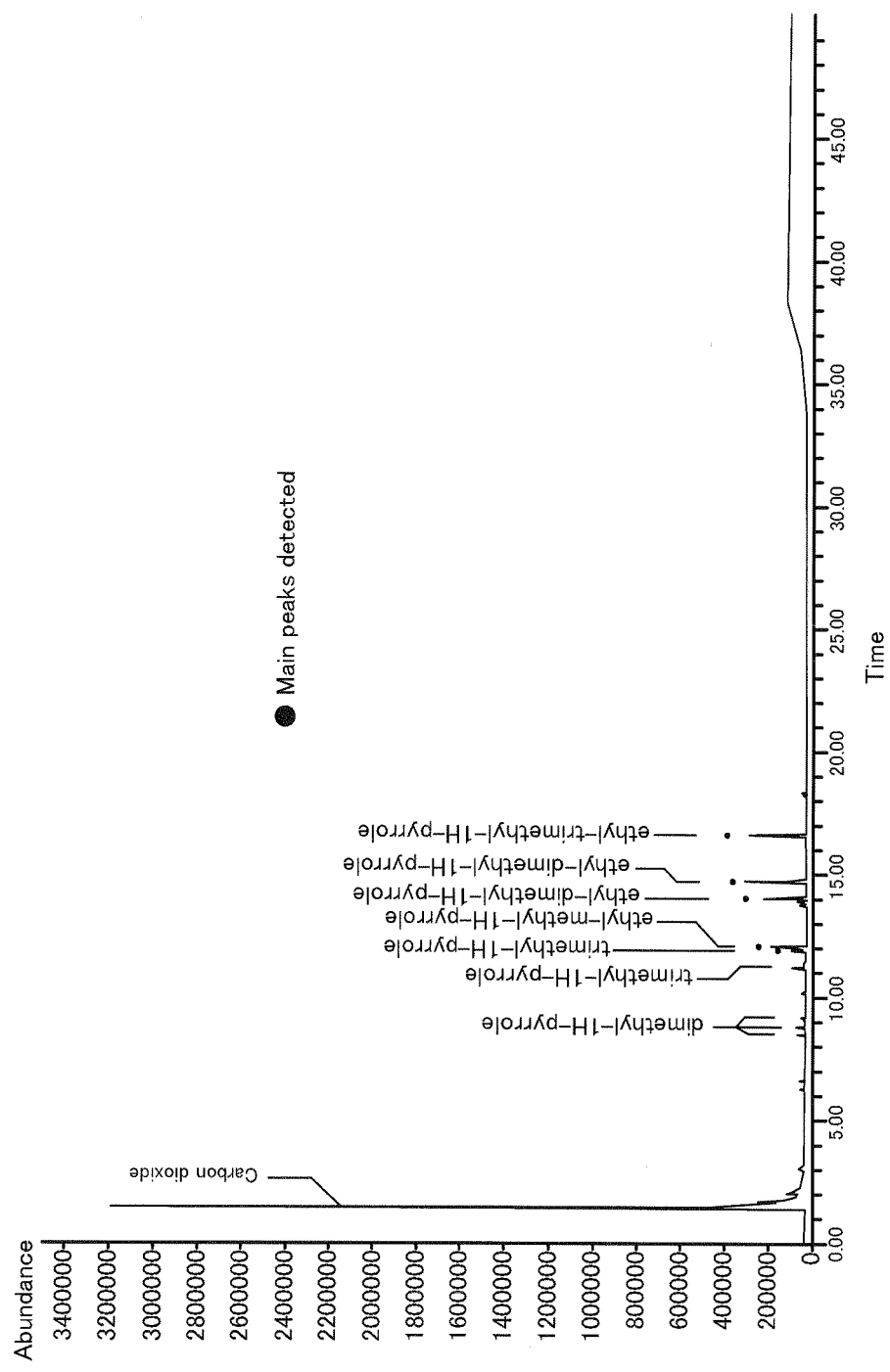
FIG. 16 shows the results of the analysis of the product prepared in Example 2, which is carried out according to the pyrolytic GC-MS technique.
Figure 17:
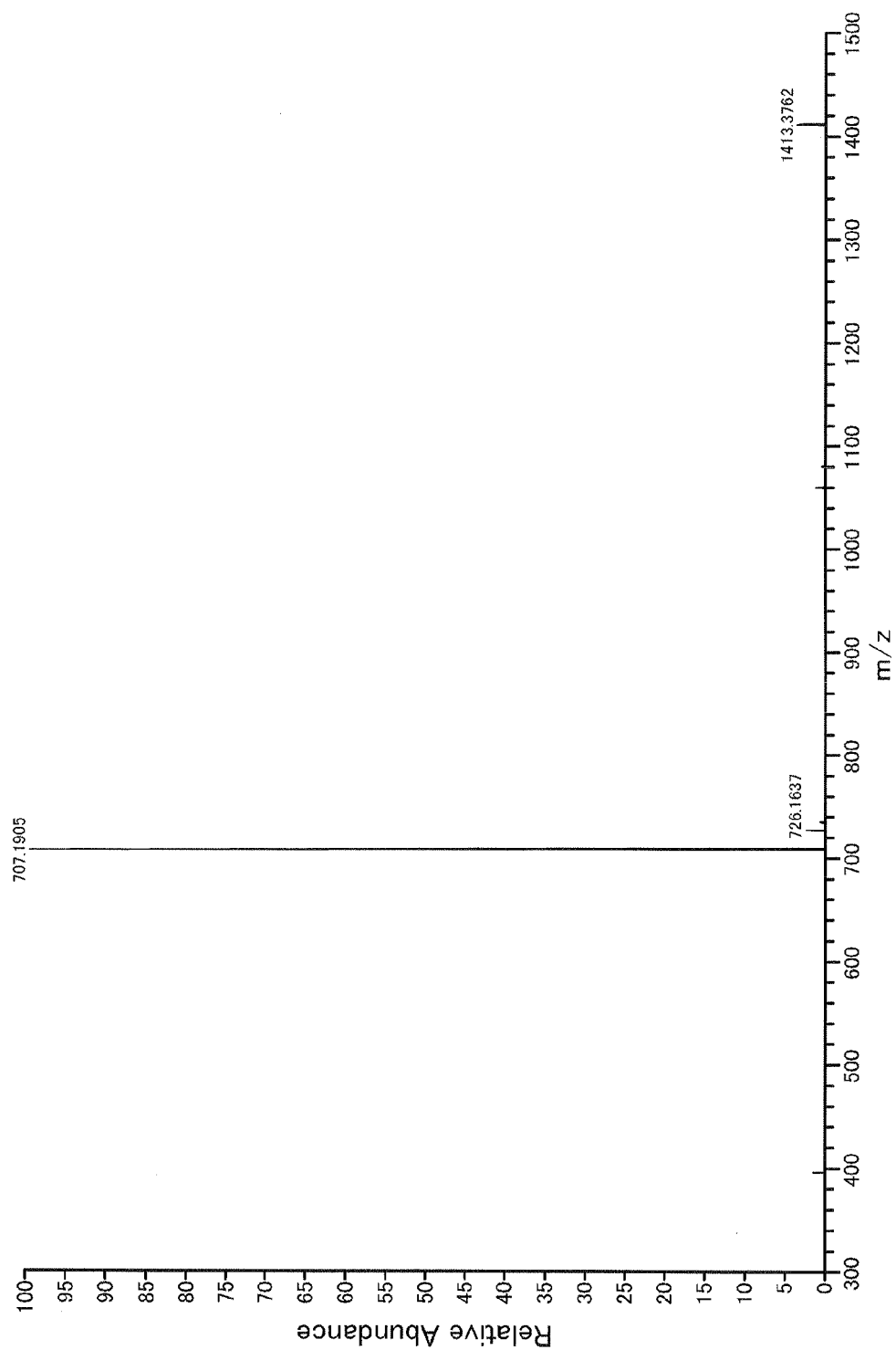
FIG. 17 shows the results of the analysis of the product prepared in Example 2, which is carried out according to the ESI-MS mass spectrometric analysis.
Figure 18:
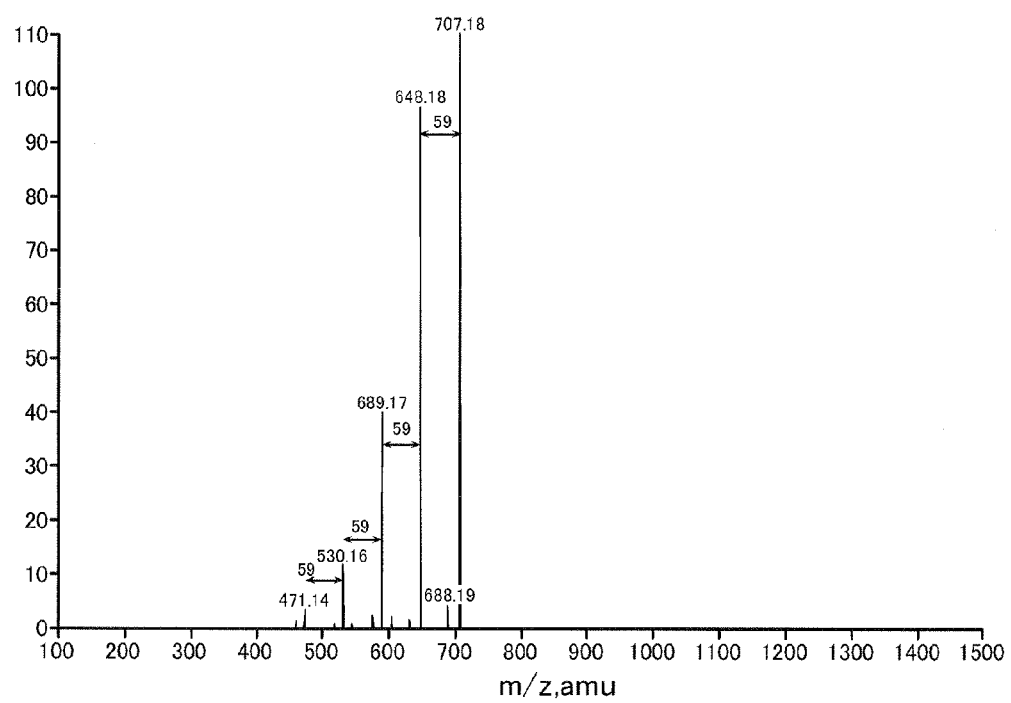
FIG. 18 shows the results of the analysis of the product prepared in Example 2, which is carried out according to the MS/MS measurement.
Figure 19:
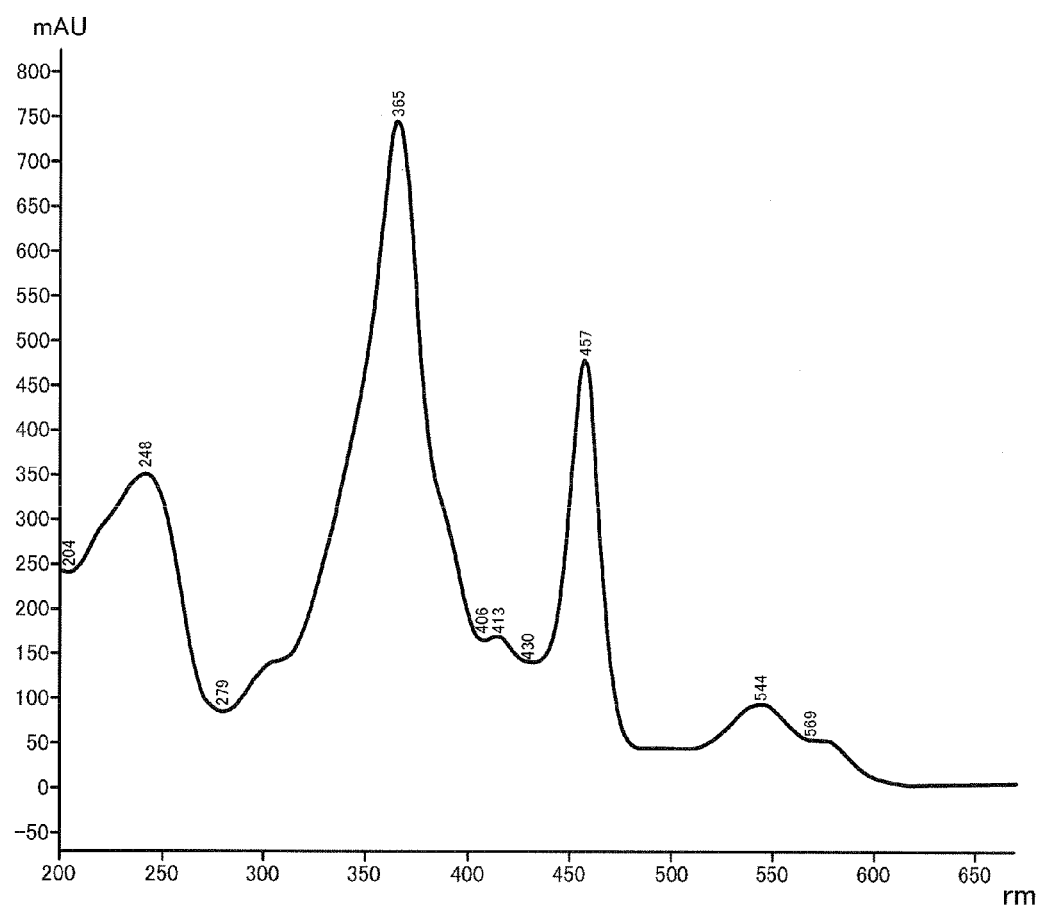
FIG. 19 shows the absorption spectrophotometric spectrogram observed for the product produced in Example 2.
Figure 20:
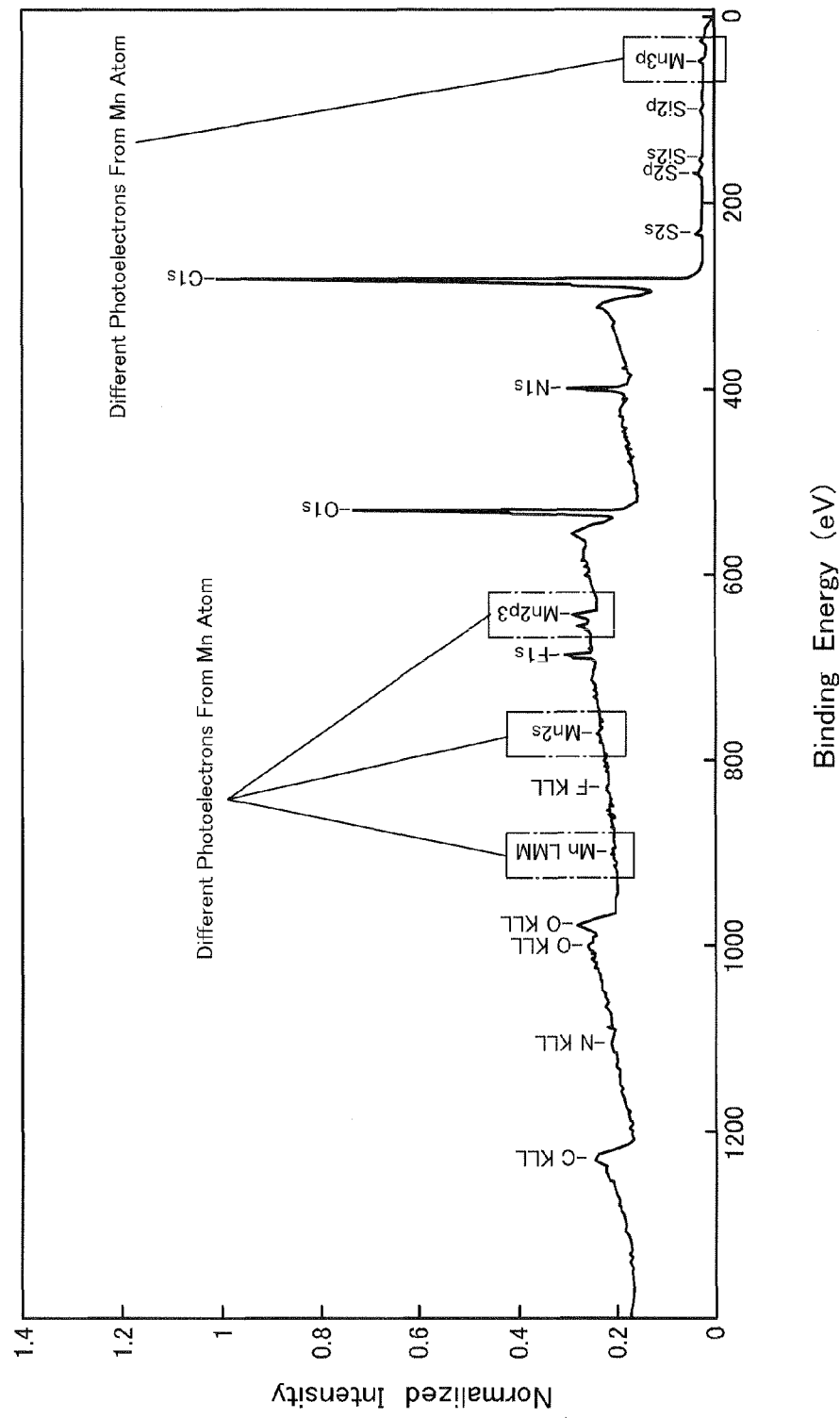
FIG. 20 shows the results of the analysis of the product prepared in Example 2, which is carried out according to the XPS elemental analysis.
Figure 21:
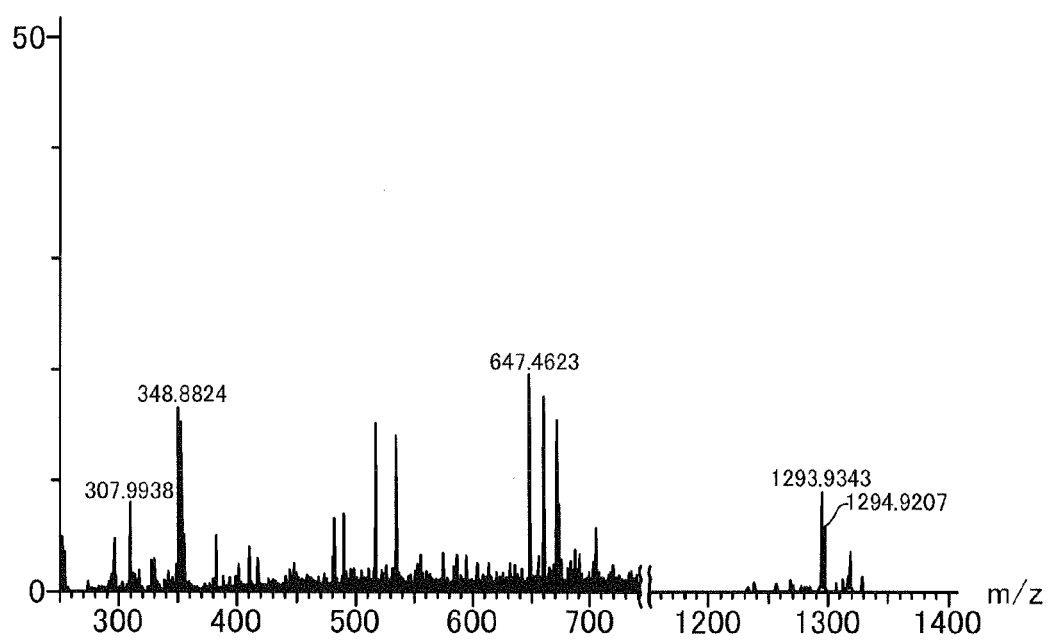
FIG. 21 shows the mass spectrometric spectrogram (TOF-MS) observed for the cultured product which is tinged with green color tone and which is produced in Example 5.
Figure 22:
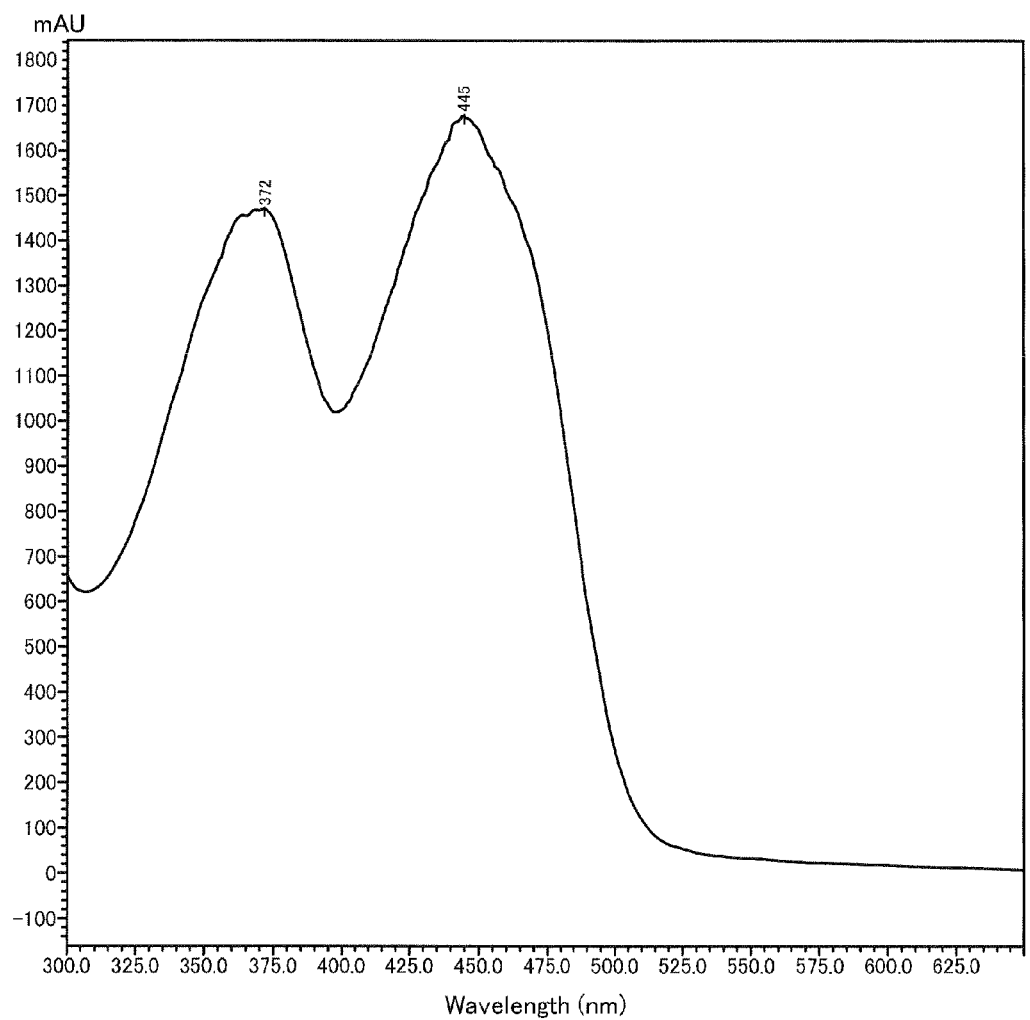
FIG. 22 is a graph showing the absorption spectrophotometric curve observed for the product which is tinged with green color tone and which is produced in Example 5.

What is claimed is:

1. A method for the production of a tetrapyrrole compound characterized in that bacterial cells of *Escherichia coli*, which cannot express the gene ypjD (b2611) due to the variation thereof, selected from the group consisting of K12, BL21, and JD23504 are cultivated in a culture medium and that the resulting tetrapyrrole compound having a porphyrin ring structure is obtained from the culture medium.

2. The method for the production of a tetrapyrrole compound as set forth in claim 1, wherein it comprises the steps of adding, to the culture medium, a metallic element capable of being converted into ions thereof in the culture medium or a metallic element-containing compound capable of being dissociated into its ions therein, as a raw material, and then collecting or isolating the resulting tetrapyrrole compound containing the metal.

3. The method for the production of a tetrapyrrole compound as set forth in claim 1 or 2, wherein the tetrapyrrole compound is one which carries four methyl groups, and four ethyl ester groups or acetate groups (propionate groups) on the porphyrin ring.

4. A method for the production of a tetrapyrrole compound characterized in that it comprises the steps of cultivating bacterial cells of *Escherichia coli*, which cannot express the gene ypjD (b2611) due to the variation thereof, selected from the group consisting of K12, BL21, and JD23504 in a culture medium which comprises, as a raw material, elemental Mn capable of being converted into ions thereof in the culture medium or an Mn-containing compound capable of being dissociated into its ions therein and then collecting or isolating, from the culture medium, the resulting tetrapyrrole compound having a porphyrin ring structure in which Mn is coordinated at the center thereof.

* * * * *